(12) United States Patent
McDougall et al.

(10) Patent No.: US 8,598,198 B2
(45) Date of Patent: Dec. 3, 2013

(54) NUCLEIC ACID BINDING DYES AND USES THEREFOR

(75) Inventors: Mark McDougall, Arroyo Grande, CA (US); Stephen Dwight, Arroyo Grande, CA (US)

(73) Assignee: Promega Corporation, Madison, WI (US)

( * ) Notice: Subject to any disclaimer, the term of this patent is extended or adjusted under 35 U.S.C. 154(b) by 452 days.

(21) Appl. No.: 12/725,251

(22) Filed: Mar. 16, 2010

(65) Prior Publication Data

US 2010/0233710 A1    Sep. 16, 2010

Related U.S. Application Data

(60) Provisional application No. 61/160,566, filed on Mar. 16, 2009.

(51) Int. Cl.
*C07D 491/06* (2006.01)
*C07D 417/06* (2006.01)

(52) U.S. Cl.
USPC ............................ 514/296; 546/94; 546/96

(58) Field of Classification Search
USPC .......................... 546/94, 96; 514/296
See application file for complete search history.

(56) References Cited

U.S. PATENT DOCUMENTS

| | | | |
|---|---|---|---|
| 2,269,234 | A | 1/1942 | Sprague |
| 2,398,999 | A | 4/1946 | Brooker et al. |
| 4,665,024 | A | 5/1987 | Mansour |
| 4,683,202 | A | 7/1987 | Mullis |
| 4,965,188 | A | 10/1990 | Mullis et al. |
| 5,321,130 | A | 6/1994 | Yue et al. |
| 5,658,751 | A | 8/1997 | Yue et al. |
| 2010/0233710 | A1 | 9/2010 | McDougall |

FOREIGN PATENT DOCUMENTS

| | | |
|---|---|---|
| GB | 625245 | 6/1949 |
| WO | 2010/107816 | 9/2010 |

OTHER PUBLICATIONS

Dorwald F. A. Side Reactions in Organic Synthesis, 2005, Wiley: VCH, Weinheim p. IX of Preface.*
Brooker, L.G.S. et al., "Color and constitution. V. The absorption of unsymmetrical cyanines. Resonance as a basis for a classification of dyes," J. Am. Chem. Soc. (1942) 64:199-210.
Mao, F. et al., "Characterization of EvaGreen and the implication of its physicochemical properties for qPCR applications," BMC Biotech (2007) 7:76, 16 pages.
Mikelsons, L. et al., "Experimental and theoretical study of the interaction of single-stranded DNA homopolymers and a monomethine cyanine dye: nature of specific binding," Photochem. Photobiol. Sci. (2005) 4:798-802.
Nygren, J. et al., "The interactions between the fluorescent dye thiazole orange and DNA," Biopolymers (1998) 46:39-51.
Schweitzer, C. et al., "Selective binding and local photophysics of the fluorescent cyanine dye Pico Green in double-stranded and single-stranded DNA," Phys. Chem. Chem. Phys. (2003) 5:4911-4917.
Wittung, P. et al., "DNA-like double helix formed by peptide nucleic acid," Nature (1994) 368:561-563.
Yarmoluk, S.M. et al., "Interaction of cyanine dyes with nucleic acids. XXI. Arguments for half-intercalation model of interaction," Biopolymers (Biospectroscopy) (2001) 62:219-227.
Yarmoluk, S.M. et al., "Symmetric cyanine dyes for detecting nucleic acids," Biotechnic. Histochem. (2008) 83 (3-4):131-145.
Zipper, H. et al., "Investigations on DNA intercalculation and surface binding by SYBR Green I, its structure determination and methodological implications," Nucleic Acids Res. (2004) 32:e103, 10 pages.
International Search Report and Written Opinion for Application No. PCT/US2010/027514 dated Nov. 4, 2010 (10 pages).

* cited by examiner

*Primary Examiner* — Rita Desai
(74) *Attorney, Agent, or Firm* — Michael Best & Friedrich LLP

(57) ABSTRACT

The invention provides novel compounds and compositions of Formulas I and II, as well as methods of using them. The compounds can be used, for example, to quantify an amount of double stranded DNA in a sample subjected to nucleic acid amplification, or for real time monitoring of a nucleic acid amplification reaction. The compounds can be provided in a kit, for example, with other reagents and instructions for using the compounds and reagents.

6 Claims, 19 Drawing Sheets

| DYE | Ref SYBR- | qPCR / [dye] conditions | Std Curve | | | Ct avg Ct StdDev | | |
|---|---|---|---|---|---|---|---|---|
| | | | Slope | $R^2$ | Y (1ng) intercept | 10pg/rxn | 1ng/rxn | 100ng/rxn |
| SGI | -33 | ABPrSyBR | -3.325 | 0.998 | 28.34 | 34.9  0.294 | 28.4  0.316 | 21.6  0.085 |
| SGI | -39b | 0.4µM | -3.400 | 0.995 | 27.2 | 34.1  0.822 | 27.1  0.148 | 20.5  0.074 |
| | -40 | | -3.350 | 0.998 | 26.9 | | | |
| | -47 | | -3.410 | 0.994 | 26.5 | 33.5  0.808 | 26.2  0.037 | 19.8  0.205 |
| | -49 | | -3.396 | 0.999 | 26.9 | 33.7  0.229 | 26.9  0.141 | 20.1  0.182 |
| | -51 | | -3.366 | 0.999 | 26.7 | 33.5  0.099 | 26.7  0.058 | 20.0  0.005 |
| 3646 | -47-04 | 0.1µM | -3.068 | 0.984 | 26.1 | 32.5  1.21 | 25.8  0.148 | 20.2  0.166 |
| | | 0.15µM | -3.548 | 0.992 | 26.5 | 33.9  0.249 | 26.5  0.478 | 19.6  0.593 |
| | -38 | 0.4µM | | | | | | |
| 3654 | -38 | 0.5µM | -3.41 | 0.997 | 26.7 | 33.2 | 26.6  0.112 | 19.9  0.033 |
| | -49 | 0.75µM | -3.312 | 0.987 | 26.6 | 33.6  0.826 | 27.0  0.179 | 19.8  0.249 |
| | | | | | | 32.9  1.28 | | |

FIG. 1A

| | | | | | | | | | | | |
|---|---|---|---|---|---|---|---|---|---|---|---|
| | | 1.0 μM | -3.381 | 0.999 | 26.9 | 33.7 | 0.395 | 27.0 | 0.117 | 20.1 | 0.124 |
| | -49 | 1.25 μM | -3.674 | 0.996 | 27.9 | 35.1 | 0.834 | 28.1 | 0.131 | 20.4 | 0.29 |
| | | 1.5 μM | -3.812 | 0.992 | 28.4 | 35.7 | 0.731 | 28.9 | 0.44 | 20.5 | 0.135 |
| | -33 | 1.5 μM | -3.767 | 0.988 | 28.1 | 35.5 | 1.30 | 28.4 | 0.36 | 20.4 | 0.132 |
| 3666 | -38 | 0.4 μM <2.5 μM | | | | 34.8 | | | | | |
| | -43 | 5.0 μM | -3.491 | 0.998 | 28.6 | 35.6 | 0.428 | 28.5 | 0.154 | 21.6 | 0.158 |
| | | 6.25 μM | -3.252 | 0.995 | 28.2 | 34.7 | 0.792 | 28.3 | 0.103 | 21.7 | 0.204 |
| | | 7.50 μM | -3.412 | 0.997 | 28.4 | 35.1 | 0.507 | 28.7 | 0.221 | 21.5 | 0.105 |
| 3667 | -38 | 0.4 μM | | | | 34.1 | | | | | |
| | -41 | 0.5 μM | -3.458 | 0.999 | 27.1 | 34.1 | 0.301 | 27.0 | 0.259 | 20.2 | 0.151 |
| | -41 | 1.0 μM | -3.338 | 0.994 | 26.8 | 33.4 | 0.873 | 27.6 | 0.221 | 20.0 | 0.012 |
| | -41 | 1.25 μM | -3.548 | 0.998 | 27.6 | 34.6 | 5.93 | 27.7 | x. | 20.4 | |
| | -41 | 1.75 μM | -3.795 | 0.968 | 28.2 | 35.6 | 2.27 | 28.5 | 0.604 | 20.5 | 0.16 |
| 3675 | -38 | 0.4 μM | | | | 34.7 | | | | | |

FIG. 1B

| | | | | | | | | | | |
|---|---|---|---|---|---|---|---|---|---|---|
| 3676 | | | | | | | | | | |
| −42 | 2.50μM | −3.068 | 0.935 | 27.7 | 35.5 | . | 28.0 | . | 21.0 | . |
| −42 | 3.75μM | −3.702 | 0.998 | 28.2 | 35.8 | 1.62 | 28.1 | 0.162 | 20.8 | 0.45 |
| −42 | 5.00μM | −3.408 | 0.998 | 28.1 | 34.8 | 0.503 | 28.1 | 0.2 | 21.2 | 0.035 |
| −42 | 6.25μM | −3.326 | 0.995 | 27.9 | 34.4 | 0.667 | 28.2 | 0.108 | 21.1 | 0.261 |
| −42 | 7.50μM | −3.875 | 0.935 | 27.2 | 34.4 | 0.74 | 28.3 | 0.033 | 18.9 | 3.06 |
| −38 | 0.4μM | | | | 41.8 | | | | | |
| −44 | 2.5μM | −3.514 | 0.999 | 34.9 | 41.8 | 0.299 | 35.0 | | 27.8 | |
| −44 | 7.5μM | −3.514 | 0.904 | 31.8 | 39.5 | 1.05 | 30.9 | | 25.2 | 0.522 |

| | | | | | | | | | | |
|---|---|---|---|---|---|---|---|---|---|---|
| 3677 | | | | | | | | | | |
| −38 | 0.4μM | | | | 33.7 | | | | | |
| −40 | 0.5μM | −3.646 | 0.999 | 26.9 | 34.2 | 0.142 | 26.8 | 0.151 | 19.5 | 0.397 |
| −40 | 0.75μM | −3.322 | 0.998 | 27.4 | 34.0 | 0.80 | 27.5 | 0.25 | 20.7 | 0.3 |
| −40 | 1.0μM | −3.382 | 0.996 | 27.4 | 34.0 | 0.408 | 27.7 | 0.248 | 20.5 | 0.239 |
| −40 | 1.25μM | −4.103 | 0.997 | 28.4 | 36.7 | 0.689 | 28.3 | 0.128 | 20.3 | 0.277 |

FIG. 1C

| | | | | | | | | |
|---|---|---|---|---|---|---|---|---|
| -40 | 1.5μM | | | | | | | |
| -40 | 1.75μM | | | | | | | |
| -40 | 2.0μM | | | | | | | |
| 3678 -38 | 0.4μM | | | 33.4 | | | | |
| -39b | 0.5μM | -3.400 | 0.995 | 27.2 | 34.0 | 0.822 | 27.1 | 0.148 | 20.5 | 0.074 |
| -39b | 0.75μM | -3.303 | 0.997 | 27.2 | 34.0 | 0.643 | 27.0 | 0.123 | 20.7 | 0.171 |
| -39b | 1.0μM | -3.383 | 0.999 | 26.8 | 33.6 | 0.383 | 26.9 | 0.217 | 20.0 | 0.040 |
| -39b | 1.25μM | -3.247 | 0.996 | 26.9 | 33.2 | 0.239 | 27.3 | 0.131 | 20.3 | 0.19 |
| -39b | 1.50μM | -3.51 | 0.997 | 27.6 | 34.5 | 0.532 | 27.7 | 0.254 | 20.5 | 0.21 |
| -39b | 1.75μM | -3.74 | 0.970 | 28.1 | 35.7 | 2.24 | 27.9 | 0.219 | 20.7 | 0.098 |
| -39b | 2.00μM | -3.39 | 0.993 | 27.5 | 34.0 | 0.423 | 28.0 | 0.234 | 20.5 | 0.355 |
| 3679 -38 | 0.4μM | | | | 37 | | | | |
| -48 | 1.0μM | -3.447 | 0.977 | 36.0 | 43.1 | 1.4 | 35.4 | 0.636 | 29.3 | 0.526 |
| -48 | 2.0μM | -3.761 | 0.977 | 35.1 | 43.0 | 1.92 | 34.8 | 1.03 | 27.8 | 0.312 |

FIG. 1D

| | | | | | | | | |
|---|---|---|---|---|---|---|---|---|
| 3699 | -50 | 0.25μM | -3.599 | 0.999 | 32.8 | 40.0, 0.236. | 32.74, 0.04. | 25.62, 0.163. |
| | | 1.00μM | -3.61 | 0.997 | 28.3 | 35.6, 0.445 | 28.03, 0.35 | 21.20, 0.174 |
| | | 1.75μM | -3.85 | 0.55 | 24.8 | 33.53, 0.32. | 27.6. | 20.18. |
| 3709 | -51 | 0.25μM | -3.51 | 0.998 | 31.8 | 38.9, 5.87 | 31.6, 5.87 | 24.9, 5.87 |
| | | 1.25μM | -3.17 | 0.979 | 29.2 | 35.2, 5.51 | 29.0, 5.51 | 22.7, 5.51 |
| | | 1.50μM | -3.49 | 0.909 | 30.0 | 37.5, 6.34 | 29.0, 6.34 | 23.5, 6.34 |
| | | 1.75μM | -4.40 | 0.990 | 29.8 | 38.3, 7.38 | 30.3, 7.38 | 20.8, 7.38 |
| 3711 | -52 | 0.25μM | -3.50 | 0.999 | 29.5 | 36.5, 0.39 | 29.6, 0.08 | 22.5, 0.18 |
| | | 0.50μM | -3.74 | 0.984 | 35.9 | 43.8, 1.54 | 35.3, 0.58 | 28.6, 0.37 |
| | | 1.00μM | -3.86 | 0.983 | 32.2 | 39.7, 0.43 | 32.3, 0.13 | 24.3, 1.69 |
| | | 1.50μM | -4.27 | 0.978 | 29.6 | 37.7, 1.63 | 30.6, 0.26 | 20.6, 0.38 |

FIG. 1E

| DYE | Expt SYBR-- | [1x Dye] In qPCR | $F_i$ Initial Fluorescence (Avg of triplicates) | | | | S | $F_M$ | $B_{ds}$ ($F_M \cdot F_i$) | $F_B$ |
|---|---|---|---|---|---|---|---|---|---|---|
| | | | NTC | 10pg [0.2 ng/mL] | 1ng [20 ng/mL] | 100ng [2 μg/mL] | | | | |
| SGI | --33 | ABPrSYBR | 3.8e4 | 4e4 | 4e4 | 8e4 | 4.2 | 1.05e6 | 27.7 | 3.6 |
| SGI | --39b | 0.4μM | 8e4 | 8e4 | 8e4 | 1.9e5 | 10 | 9.4e5 | 11.8 | 8.5 |
| | --40 | 0.4μM | 7.8e4 | | | | | 9.9e5 | 12.7 | 7.9 |
| | --42 | 0.4μM | 7.7e4 | 7e4 | 1e5 | 1.9e5 | 11.3 | | | |
| | --49 | 0.4μM | 7e4 | 7e4 | 7e4 | 2e5 | 13.0 | 1.1e6 | 15.7 | 6.4 |
| 3508 | | | | | | | | | | |
| 3046 | --47-04 | 0.10μM | 2e4 | 2e4 | 3e4 | 4.5e4 | 2.5 | 2.4e5 | 12.0 | 8.3 |
| | | 0.15μM | 3e4 | 3e4 | 3e4 | 7e4 | 4.0 | 3.4e5 | 8.0 | 12.5 |
| 3654 | --38 | 0.4μM | | | | | | | | |
| | | 0.5μM | 6e4 | 6e4 | 7.3e4 | 1.45e5 | 8.5 | 6.3e5 | 10.5 | 9.5 |
| | --49 | 0.75μM | 1e5 | 1e5 | 1e5 | 2e5 | 10 | 9.4e5 | 9.4 | 10.6 |

FIG. 2A

| | | | | | | | | | | |
|---|---|---|---|---|---|---|---|---|---|---|
| | −49 | 1.0μM | 1.2e5 | 1.2e5 | 1.5e5 | 2e5 | 8.0 | 1.07e6 | 7.13 | 14.0 |
| | −49 | 1.25μM | 1.4e5 | 1.4e5 | 1.4e5 | 2.7e5 | 13 | 1.25e6 | 8.9 | 11.2 |
| | −49 | 1.5μM | 1.6e5 | 1.6e5 | 1.6e5 | 4e5 | 24 | 1.7e6 | 10.6 | 9.4 |
| | −33 | 1.5μM | 1.6e5 | 1.6e5 | 1.6e5 | 4.5e5 | 39 | 1.3e6 | 8.1 | 12.3 |
| 3666 | −38 | 0.4μM | | | | | | | | |
| | −43 | 5.0μM | 2.4e5 | 2.3e5 | 2e5 | 2e5 | u | 5.7e5 | 2.4 | 42.1 |
| | −43 | 6.25μM | 2.7e5 | 2.7e5 | 2.7e5 | 3.1e5 | 4 | 7.3e5 | 2.7 | 37.0 |
| | −43 | 7.5μM | 3.2e5 | 2.8e5 | 2.8e5 | 3.3e5 | u | 8.7e5 | 2.7 | 36.8 |
| 3667 | −38 | 0.4μM | | | | | | | | |
| | −41 | 0.5μM | 1.3e5 | 1.3e5 | 1.3e5 | 2e6 | 7 | 9e5 | 6.9 | 14.4 |
| | −41 | 1.0μM | 2.2e5 | 2.2e5 | 2.2e5 | 3e5 | 8 | 1.4e6 | 6.4 | 15.7 |
| | −41 | 1.25μM | 2.7e5 | 2.7e5 | 2.7e5 | 4e5 | 13 | 1.8e6 | 6.6 | 15.0 |
| | −41 | 1.75μM | 3.3e5 | | | 5e5 | 17 | 2e6 | 7.9 | 12.7 |
| 3675 | −38 | 0.4μM | | | | | | | | |
| | −42 | 2.50μM | 1e5 | 1e5 | 1e5 | 1.2e5 | 2 | 4.3e5 | 4.3 | 23.3 |

FIG. 2B

| | | | | | | | | | |
|---|---|---|---|---|---|---|---|---|---|
| | −42 | 3.75 μM | 1.6e5 | 1.8e5 | 1.9e5 | 2.0e5 | 4 | 6.3e5 | 3.9 | 25.4 |
| | −42 | 5.00 μM | 1.8e5 | 2.1e5 | 2.2e5 | 2.3e5 | 5 | 7.1e5 | 3.9 | 25.4 |
| | −42 | 6.25 μM | 2.3e5 | 2.2e5 | 2.3e5 | 3e5 | 7 | 9.6e5 | 4.2 | 24.0 |
| | −42 | 7.50 μM | 2.7e5 | 2.7e5 | 2.5e5 | 3.2e5 | 5 | 1.1e6 | 4.1 | 24.5 |
| 3676 | −38 | 0.4 μM | | | | | | | | |
| | −44 | 2.5 μM | 4.3e5 | 4e5 | 4.5e5 | 4.5e5 | 2. | 9.2e5 | 2.1 | 46.7 |
| | −44 | 7.5 μM | 1e6 | 9e5 | 9e5 | 1.1e6 | 10 | 2.5e5 | 2.5 | 40 |
| 3677 | −40 | 0.50 μM | 1.3e5 | 1.5e5 | 1.5e5 | 2.2e5 | 9 | 8.0e5 | 6.2 | 16.3 |
| | −40 | 0.75 μM | 1.9e5 | 2e5 | 2.2e5 | 2.8e5 | 9 | 1.2e6 | 6.3 | 15.8 |
| | | 1.0 μM | 2.2e5 | 2.2e5 | 2.5e5 | 3.3e5 | 11 | 1.3e6 | 5.9 | 16.9 |
| | | 1.25 μM | 2.8e5 | 2.8e5 | 2.8e5 | 4.5e5 | 17. | 1.8e6 | 6.4 | 15.6 |
| | | 1.5 μM | 3.7e5 | | | 5.8e5 | 21. | 2.1e6 | 5.7 | 17.6 |
| | | 1.75 μM | | | | | | | | |
| 3678 | −38 | 0.4 μM | 9.5e4 | 1.0e5 | 8.0e4 | 1.3e5 | | 1e6 | 12.5 | 8.0 |
| | −39b | 0.5 μM | 8.0e4 | 8.0e4 | 8.0e4 | | | | | 8.0 |

FIG. 2C

| | | | | | | | | | | |
|---|---|---|---|---|---|---|---|---|---|---|
| | −39b | 0.75µM | 1.3e5 | 1.5e5 | 1.8e5 | 2e5 | 5 | 1.5e6 | 11.5 | 8.7 |
| | −39b | 1.0µM | 1.5e5 | 1.75e5 | 1.8e5 | 2.3e5 | 7 | 1.6e6 | 10.7 | 9.3 |
| | −39b | 1.25µM | 1.9e5 | 1.9e5 | 2e5 | 3.5e5 | 8 | 2.1e6 | 11.1 | 9.0 |
| | −39b | 1.50µM | 2.2e5 | 2.0e5 | 2.0e5 | 4.0e5 | 16 | 2.2e6 | 10.0 | 10 |
| | −39b | 1.75µM | 2.2e5 | 2.2e5 | 2.2e5 | 4.5e5 | 18 | 2.4e6 | 10.9 | 9.2 |
| | −39b | 2.0µM | 2.5e5 | 2.5e5 | 2.5e5 | 5.5e5 | 23 | 2.6e6 | 10.4 | 9.6 |
| 3679 | −38 | 0.4µM | 1.5e5 | 1.5e5 | | | 30 | | | |
| | −48 | 1.0µM | 2.8e5 | 2.8e5 | 3.2e5 | 2.8e5 | 0.5 | 4.6e5 | 1.6 | 60.9 |
| | −48 | 2.0µM | 4.3e5 | 5.3e5 | 5.3e5 | 4.6e5 | 9 | 8.2e5 | 1.9 | 52.4 |
| 3699 | −50 | 0.25µM | 1.4e5 | 1.4e5 | 1.4e5 | 1.45e5 | 15 | 3.6e5 | 2.6 | 38.9 |
| | | 1.00µM | 3.9e5 | 3.9e5 | 4.0e5 | 4.8e5 | | 1.2e6 | 3.1 | 32.5 |
| | | 1.75µM | 6.0e5 | 6.0e5 | 6.5e5 | 7.5e5 | | 1.99e6 | 3.3 | 30.2 |
| 3709 | −51 | 0.25µM | 1.8e5 | 1.8e5 | 1.8e5 | 1.8e5 | | 2.98e5 | 1.7 | 60.4 |

FIG. 2D

| | | 1.25μM | 6.5e5 | 6e5 | 6.5e5 | 6.8e5 | | 1.16e6 | 1.7 | 60.3 |
|---|---|---|---|---|---|---|---|---|---|---|
| | | 1.50μM | 7.5e5 | 7e5 | 7.5e5 | 7.8e5 | 3 | 1.39e6 | 1.9 | 54 |
| | | 1.75μM | 8.2e5 | 9e5 | 8.6e5 | 9.5e5 | 3 | 1.73e6 | 2.1 | 47.4 |
| | | | | | | | 13 | | | |
| 3711 | −52 | 0.25μM | 6e4 | 6e4 | 6e4 | 6e4 | | 1.5e5 | 2.5 | 40.0 |
| | | 0.50μM | 1.5e5 | 1.5e5 | 1.5e5 | 1.5e5 | | 2.7e5 | 1.8 | 55.6 |
| | | | | | | | | | | |

FIG. 2E

| DYE | Ref SYBR-- | qPCR conditions | ΔR max N T C | 10 pg/rxn | 1 ng/rxn | 100 ng/rxn |
|---|---|---|---|---|---|---|
| SGI | --33 | ABPtSYBR | -- | 5.3e5 | 7.5e5 | 1e6 |
| SGI | --39b | 0.40μM | -- | 8e5 | 8.5e5 | 8.5e5 |
|  | --40 |  |  |  |  |  |
|  | --41 |  |  |  |  |  |
|  | --42 |  |  |  |  |  |
|  | --43 |  |  |  |  |  |
|  | --44 |  |  |  |  |  |
|  | --45 |  |  |  |  |  |
|  | --46 |  |  |  |  |  |
|  | --47 |  |  |  |  |  |
|  | --48 |  |  |  |  |  |
|  | --49 | 0.40μM |  | 8e5 | 9.0e5 | 9.5e5 |
|  | --50 |  |  |  |  |  |
|  | --51 |  |  |  |  |  |
|  | --52 |  |  |  |  |  |
| 3568 | --38 | 0.4μM |  |  |  |  |
| 3646 | --47-04 | 0.10 μM | -- | 1.6e5 | 1.9e5 | 1.2e5 |
|  |  | 0.15 μM | -- | 2.3e5 | 2.8e5 | 2e5 |
| 3654 | --38 | 0.4μM |  |  |  |  |
|  | --49 | 0.5μM |  | 3.4e5 | 5e5 | 5.2e5 |
|  | --49 | 0.75μM |  | 5.5e5 | 6e5 | 7e5 |
|  | --49 | 1.0μM |  | 5.8e5 | 8.2e5 | 8.2e5 |

FIG. 3A

| | | | | | |
|---|---|---|---|---|---|
| | -49 | 1.25μM | 5.7e5 | 9e5 | 1.1e6 |
| | -49 | 1.5μM | 7e5 | 9e5 | 1.5e5 |
| | -33 | 1.5μM | 7.6e5 | 1.1e6 | 1.6e6 |
| 3666 | -38 | 0.4μM | | xx | |
| | -43 | 5.0μM | 1.2e5 | 3e5 | 3.8e5 |
| | | 6.25μM | 1.6e5 | 3.2e5 | 4.8e5 |
| | -43 | 7.50μM | 2e5 | 4e5 | 5.4e5 |
| 3667 | -38 | 0.4μM | | | |
| | -41 | 0.5μM | 4.8e5 | 6.8e5 | 7e5 |
| | | 1.0μM | 7.5e5 | 1.2e6 | 1.1e6 |
| | | 1.25μM | | | |
| | | 1.75μM | 9e5 | 1.5e6 | 1.8e6 |

| | | | | | |
|---|---|---|---|---|---|
| 3675 | -38 | 0.4μM | 1.8e5 | 2.4e5 | 3.1e5 |
| | -42 | 2.50μM | 2.2e5 | 4.5e5 | 4.1e5 |
| | | 3.75μM | 2.2e5 | 4.5e5 | 4.7e5 |
| | | 5.00μM | 3e5 | 5.8e5 | 7e5 |
| | | 6.25μM | 3.5e5 | 5.5e5 | 8.3e5 |
| 3676 | -38 | 0.4μM | | | |
| | -44 | [2.5-10uM] | | | |
| | | 2.50μM | 1.7e5 | 4e5 | 4e5 |
| | | 7.50μM | 3.2e5 | 6.7e5 | 2.3e5 |
| 3677 | -38 | 0.4μM | | | |
| | -40 | 0.5μM | 3.8e5 | 6.8e5 | 6.5e5 |
| | | 0.75μM | 6e5 | 9.8e5 | 9e5 |
| | | 1.0μM | 6e5 | 1e6 | 1.1e6 |
| | | 1.25μM | 6e5 | 1.15e5 | 1.45e5 |
| | | 1.5μM | 7e5 | 1.1e6 | 1.7e6 |

FIG. 3B

| | | 1.75μM | | | |
|---|---|---|---|---|---|
| 3678 | --38 | 0.4 μM | 4.5e5 | 8e5 | 7.7e5 |
| | --39b | 0.5 μM | 5e5 | 1.3e6 | 1.1e6 |
| | --39b | 0.75 μM | 7.5e5 | 1.3e6 | 1.3e6 |
| | --39b | 1.0μM | 7.5e5 | 1.43e6 | 1.85e6 |
| | --39b | 1.25μM | 9e5 | 1.4e6 | 2e6 |
| | --39b | 1.50μM | 1e6 | 1.6e6 | 2e6 |
| | --39b | 1.75μM | 1.1e6 | 1.6e6 | 2.22e6 |
| | --39b | 2.00μM | 9.5e5 | 1.4e6 | |
| 3679 | --38 | 0.4 μM | | <xx | 1.6e5 |
| | --48 | 1.0 μM | 3.8e4 | 7e4 | 2.8e5 |
| | --48 | 2.0 μM | 5.0e4 | 1.1e5 | |
| 3699 | --50 | 0.25μM | 1e5 | 2e5 | 2.5e5 |
| | | 1.00μM | 2.5e5 | 4.8e5 | 7.0e5 |
| | | 1.75μM | 4.2e5 | 7e5 | 1.1e6 |
| 3709 | --51 | 0.25μM | 4e4 | 1e5 | 1.5e5 |
| | | 1.25μM | 2e5 | 3.3e5 | 5.8e5 |
| | | 1.50μM | 2.5e5 | 4e5 | problem |
| | | 1.75μM | 3e5 | 4.5e5 | 6.5e5 |
| 3711 | --52 | 0.25μM | 3.8e4 | 6.5e4 | 7.5e4 |
| | | 0.50μM | 7e4 | 1.3e5 | 1.5e5 |
| | | 1.00μM | 1.2e5 | 2.5e5 | 4e5 |
| | | 1.50μM | 1e5 | 3.2e5 | 6.5e5 |

FIG. 3C

| DYE | Ref | $\phi$ Quantum Yield | [μM] *1X in qPCR | $\Delta R_{max}$ Real Fluorescence 10pg amps at end of 45 cycles ≥5e5 | Ct 10pg ≤35 | M Std Curve Slope -3.0→-3.5 | Y Std Crv Y intercept (=1ng) ≤29 | S Relative Sensitivity Factor ≥4 | $B_{ds}$ Brightness ≈ ≥10% | $F_B$ Background Fluorescence ≈ ≤10% |
|---|---|---|---|---|---|---|---|---|---|---|
| AB Power SYBR | --33 | nd | nd | 5.3e5 | 34.9 | -3.325 | 28.34 | 4.2 | 27.7 | 3.6 |
| SGII | --39h | 0.73 | 0.4 | 8.0e5 | 33.3 | -3.40 | 27.2 | 12 | 11.8 | 8.5 |
| 3646 | --47<br>--38 | 0.43 | 0.1<br>0.15<br>0.4 | < 5.5e5 | 32.5<br>33.9<br>nd | -3.064<br>-3.548<br>> | 26.1<br>26.5 | 4.0 | 12.0<br><<br>< | 8.3<br>><br>> |
| 3654 | --38<br>--49 | 0.70 | 0.4<br>0.5<br>0.75 | 5.5e5 | 33.2<br>33.5<br>32.9 | -3.41<br>-3.312 | 26.7<br>26.6 | 8.5<br>10 | 10.5<br>9.4 | 9.5<br>10.6 |
|  | --33 |  | 1.0<br>1.25<br>1.5<br>1.5 | 5.8e5<br>5.7e5<br>7.0e5<br>7.6e5 | 33.7<br>35.1<br>35.7<br>35.5 | -3.381<br>><br>><br>> | 26.9<br>27.9<br>28.4<br>28.1 | 8.0<br>13<br>24<br>39 | (7.1)<br>(8.9)<br>10.6<br>(8.1) | (14.0)<br>(11.2)<br>9.4<br>(12.3) |

FIG. 4A

| | | | | | | | | | |
|---|---|---|---|---|---|---|---|---|---|
| 3666 | −38 −43 | 0.34 | 0.4 5.0 6.25 7.50 | | 34.8 > 34.7 > | . −3.49 −3.25 −3.41 | . 28.6 28.2 28.4 | . . 4 . | . > > > | . > > > |
| 3667 | −38 −41 | 0.68 | 0.4 0.5 1.0 | 4.8e5 7.5e5 | 34.1 34.1 33.4 | . −3.46 −3.34 | . 27.1 26.8 | . 7 8 | . (6.9) (6.4) | . (14.4) (15.7) |
| | | | 1.25 1.75 | 9.0e5 | 34.6 > | −3.55 | 27.6 28.2 | 13 17 | (6.6) (7.9) | (15.0) (12.7) |
| 3675 | −38 −42 | 0.31 | 0.4 2.5 3.75 5.0 6.25 | | 34.7 > > 34.8 34.4 | −3.07 . −3.41 −3.33 | 27.7 28.2 28.1 27.9 | . 4 5 7 | . > > > | . > > > > |
| 3676 | −38 −44 | 0.48 | 0.4 2.5 7.5 | | > > > | −3.51 −3.51 | | . 10 | . > > | . > > |
| 3677 | −38 −40 | 0.72 | 0.4 0.5 0.75 1.0 | 6e5 6e5 | 33.7 34.2 34.0 34.0 | −3.32 −3.38 | 26.9 27.4 27.4 | 9 9 11 | (6.2) (6.3) (5.9) | (16.3) (15.8) (16.9) |
| | | | 1.25 1.5 | 6e5 7e5 | > | | 28.4 | 17 21 | (6.4) (5.7) | (15.6) (17.6) |

FIG. 4B

| | | | | | | | | | |
|---|---|---|---|---|---|---|---|---|---|
| 3678 | --38 -- 39b | 0.68 | 0.4 0.5 0.75 1.0 1.25 1.50 1.75 2.00 | 4.5e5 5e5 7.5e5 7.5e5 9e5 1e6 1.1e6 9.5e5 | 33.4 34.0 34.0 33.6 33.2 34.5 35.7 34.0 | -3.40 -3.30 -3.38 -3.25 -3.51 > -3.39 | 27.2 27.2 26.8 26.9 27.6 28.1 27.5 | 5 7 8 16 18 23 30 | . 12.5 11.5 10.7 11.1 10.0 10.9 10.4 | . 8.0 8.7 9.3 9.0 10.0 9.2 9.6 |
| 3679 | --38 --48 | 0.34 | 0.4 1.0 | | > > | -3.45 | | . | V | ^ |
| 3699 | --50 | | 0.25 1.0 1.75 | | > > 33.5 | -3.599 | 28.3 24.8 | . 9 15 | . V V | . ^ ^ |
| 3709 | --51 | | 0.25 1.25 1.5 1.75 | | > > > | -3.51 -3.17 | | . . 13 | V V V | ^ ^ ^ |
| 3711 | --52 | | 0.25 0.5 1.0 1.5 | | > > > > | -3.5 | | . . 10 | V V V | ^ ^ ^ |

\* some stock concentrations were designed without considering the TFA salt.

FIG. 4C

| DYE | DYE Concentration | STANDARD CURVE | | |
|---|---|---|---|---|
| | | Slope | $R^2$ | Y intercept |
| 3646 | 0.1 μM | -3.068 | 0.984 | 26.1 |
| | 0.15 μM | -3.548 | 0.992 | 26.5 |
| 3654 | 0.5 μM | -3.41 | 0.997 | 26.7 |
| | 0.75 μM | -3.312 | 0.987 | 26.6 |
| | 1.0 μM | -3.381 | 0.999 | 26.9 |
| | 1.25 μM | -3.674 | 0.996 | 27.9 |
| | 1.5 μM | -3.812 | 0.992 | 28.4 |
| | 1.5 μM | -3.767 | 0.988 | 28.1 |
| 3666 | 5.0 μM | -3.491 | 0.998 | 28.6 |
| | 6.25 μM | -3.252 | 0.995 | 28.2 |
| | 7.50 μM | -3.412 | 0.997 | 28.4 |
| 3667 | 0.5 μM | -3.458 | 0.999 | 27.1 |
| | 1.0 μM | -3.338 | 0.994 | 26.8 |
| | 1.25 μM | -3.548 | 0.998 | 27.6 |
| | 1.75 μM | -3.795 | 0.968 | 28.2 |
| 3675 | 2.50 μM | -3.068 | 0.935 | 27.7 |
| | 3.75 μM | -3.702 | 0.998 | 28.2 |
| | 5.00 μM | -3.408 | 0.998 | 28.1 |
| | 6.25 μM | -3.326 | 0.995 | 27.9 |
| | 7.50 μM | -3.875 | 0.935 | 27.2 |
| 3676 | 2.5 μM | -3.514 | 0.999 | 34.9 |
| | 7.5 μM | -3.514 | 0.904 | 31.8 |

FIG. 5

NUCLEIC ACID BINDING DYES AND USES THEREFOR

CROSS-REFERENCE TO RELATED APPLICATIONS

This application claims the benefit of U.S. Application Ser. No. 61/160,566, filed Mar. 16, 2009, which is incorporated by reference herein.

FIELD OF THE INVENTION

The invention relates to fluorescent dyes for nucleic acids. In particular, the invention relates to dyes that form a fluorescent complex in combination with double stranded nucleic acids, which can be used in detecting and quantifying nucleic acids in a wide range of materials, including biological and environmental samples.

BACKGROUND

In many fields of life sciences research, including biological, biomedical, genetic, fermentation, aquaculture, agricultural, forensic and environmental research, there is a need to identify nucleic acids, as well as quantify those nucleic acids, in pure solutions and in biological samples. Such applications require a fast, sensitive, and selective methodology that can detect minute amounts of nucleic acids in a variety of media, whether or not the nucleic acid is contained in cells.

The detection of nucleic acids by fluorescent dyes such as SYBR Green I (SG) has been applied successfully in the detection of nucleic acids in gels, in solution, in the determination of DNase or telomerase activities, in fluorescence imaging techniques, in flow cymetry, in real-time PCR, in biochip applications, and in the quantification of double stranded DNA, e.g., in crude extracts.

SG was shown to intercalate at low dye/base pair ratios (dbprs) (Zipper et al., *Nucl. Acids Res.*, 32:e103 (2004)). In agreement with most simple intercalators and the fluorescent DNA binding dye PicoGreen (PG), SG did not display a marked sequence binding preference at low dbprs, although a significant sequence dependence of SG binding was observed at high dbprs (Zipper et al.). PG was not sequence specific at low dbprs, however, at high dbprs, which are generally used for quantification of DNA in solution, PG had some sequence specificity (Zipper et al.).

Zipper et al. disclose that dbprs>0.2 should be applied to discriminate between single stranded DNA and double stranded DNA, and that for maximum double stranded DNA selectively, for instance, with respect to other compounds such as RNA, proteins, and the like, dbprs of at least 10 should be employed. It is also disclosed that the use of higher dbprs can reduce the impact of salts, quenchers and dsDNA sequence specificity, which can affect SG real-time PCR and melting curve analyses (Zipper et al.). Zipper et al. caution that inhibition of PCR as well as the potential degradation of dsDNA may occur at high dbprs and that in PCR the dbpr is not constant.

EvaGreen® (EG) is a DNA binding dye with a lower binding affinity for both double stranded DNA and single stranded DNA than SG (Mao et al., *BMC Biotech.*, 7:76 (2007)). Mao et al. disclose that EG showed no apparent preference for either GC- or AT-rich sequences while SG had a slight preference for AT-rich sequences. Both dyes showed substantially lower affinity towards single stranded DNA than toward double stranded DNA, however, both EG and SG exhibited PCR interference when used at high dye concentrations, as evident by the delayed Ct and/or nonspecific product formation (Mao et al.). Mao et al. disclose that the problem worsened when the chain extension time was shortened or when the amplicon size was relatively long (>500 bp). The differences in qPCR performance between the two dyes was attributed to their differences in DNA binding profiles (Mao et al.).

SUMMARY OF THE INVENTION

In one aspect, the present invention provides a compound of Formula I:

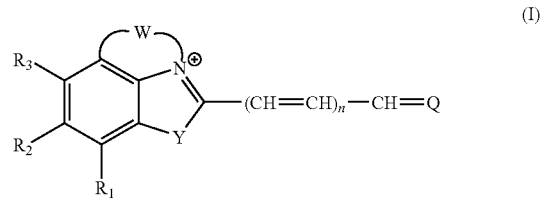

wherein
$R^1$, $R^2$ and $R^3$ are each independently H, alkyl, cycloalkyl, aryl, heteroaryl, amino, hydroxy, or halo; or $R^1$ and $R^2$, or $R^2$ and $R^3$, taken together with the atoms to which they are attached form a fused benzo ring that is optionally substituted with 1, 2, 3, or 4 alkyl, cycloalkyl, aryl, heteroaryl, amino, hydroxy, or halo groups;
Y is S, O, $CF_2$, or $NR^4$;
$R^4$ is $(C_1$-$C_8)$alkyl, aryl, or $(C_1$-$C_8)$alkaryl;
W taken together with the atoms to which it is attached is a 5-, 6-, 7-, or 8-membered heterocyclic ring;
n is 0, 1, or 2;
Q is Q1 or Q2:

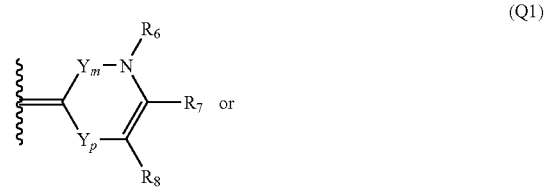

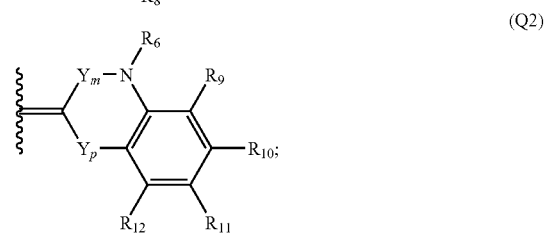

wherein
Y is —$CR^{13}$=$CR^{14}$—; m and p are 0 or 1 such that m+p=1;
$R^6$ is $(C_1$-$C_8)$alkyl, aryl, or $(C_1$-$C_8)$alkaryl;
$R^7$, $R^8$, $R^9$, $R^{10}$, $R^{11}$, and $R^{12}$ are each independently H, alkyl, cycloalkyl, aryl, heteroaryl, amino, or halo;
one of $R^{13}$ and $R^{14}$ is H and the other is $NR^{15}R^{16}$;
$R^{15}$ is $(C_1$-$C_6)$alkyl or $(C_1$-$C_6)$alkyl-$NR^{17}R^{18}$, wherein $R^{17}$ and $R^{18}$ are each independently H or $(C_1$-$C_6)$alkyl; and
$R^{16}$ is $(C_1$-$C_6)$alkyl-$NR^{17}R^{18}$, wherein $R^{17}$ and $R^{18}$ are each independently H or $(C_1$-$C_6)$alkyl;
or a salt thereof.

In another aspect, the present invention provides a method to quantify the amount of a nucleic acid in a sample subjected to nucleic acid amplification, comprising contacting the sample with a compound according to Formula I, detecting fluorescence in the amplification reaction, and correlating the amount of fluorescence in the amplification reaction with the amount of nucleic acid in the reaction.

In a further aspect, the present invention provides a method to quantify the amount of a nucleic acid in a sample subjected to nucleic acid amplification, comprising amplifying nucleic acid in a sample comprising a target nucleic acid molecule, one or more nucleic acid primers specific for target sequences to be amplified, a polymerase, and a compound of Formula I, so as to yield a mixture comprising amplified nucleic acid, detecting fluorescence in the mixture, and correlating the amount of fluorescence in the mixture with the amount of nucleic acid in the mixture.

In another aspect, the present invention provides a method of real time monitoring of a nucleic acid amplification reaction, comprising amplifying a target nucleic acid sequence in a target nucleic acid molecule in reaction mixture containing a sample having the target nucleic acid molecule, two or more nucleic acid primers specific for sequences in the target nucleic acid molecule, and a compound of Formula I, illuminating the reaction mixture with light of a selected wavelength that is absorbed by the compound, and detecting the fluorescence emission in the reaction mixture.

The present invention also provides a kit comprising a compound according to Formula I. In an additional aspect, the present invention provides a method of making compounds according to Formula I.

BRIEF DESCRIPTION OF DRAWINGS

FIG. 1. Ct and standard deviation, slope and $R^2$ for exemplary dyes.

FIG. 2. Analysis of total fluorescence in spectral view for exemplary dyes.

FIG. 3. $\Delta R^2$max at 45 cycles for various dyes.

FIG. 4. $\Delta R$max, Ct, slope, X-intercept, S, $B_{ds}$, and $F_B$ data for various dyes.

FIG. 5. Slope, $R^2$ and Y-intercept for exemplary dyes.

DETAILED DESCRIPTION OF THE INVENTION

Definitions

Figure 6:
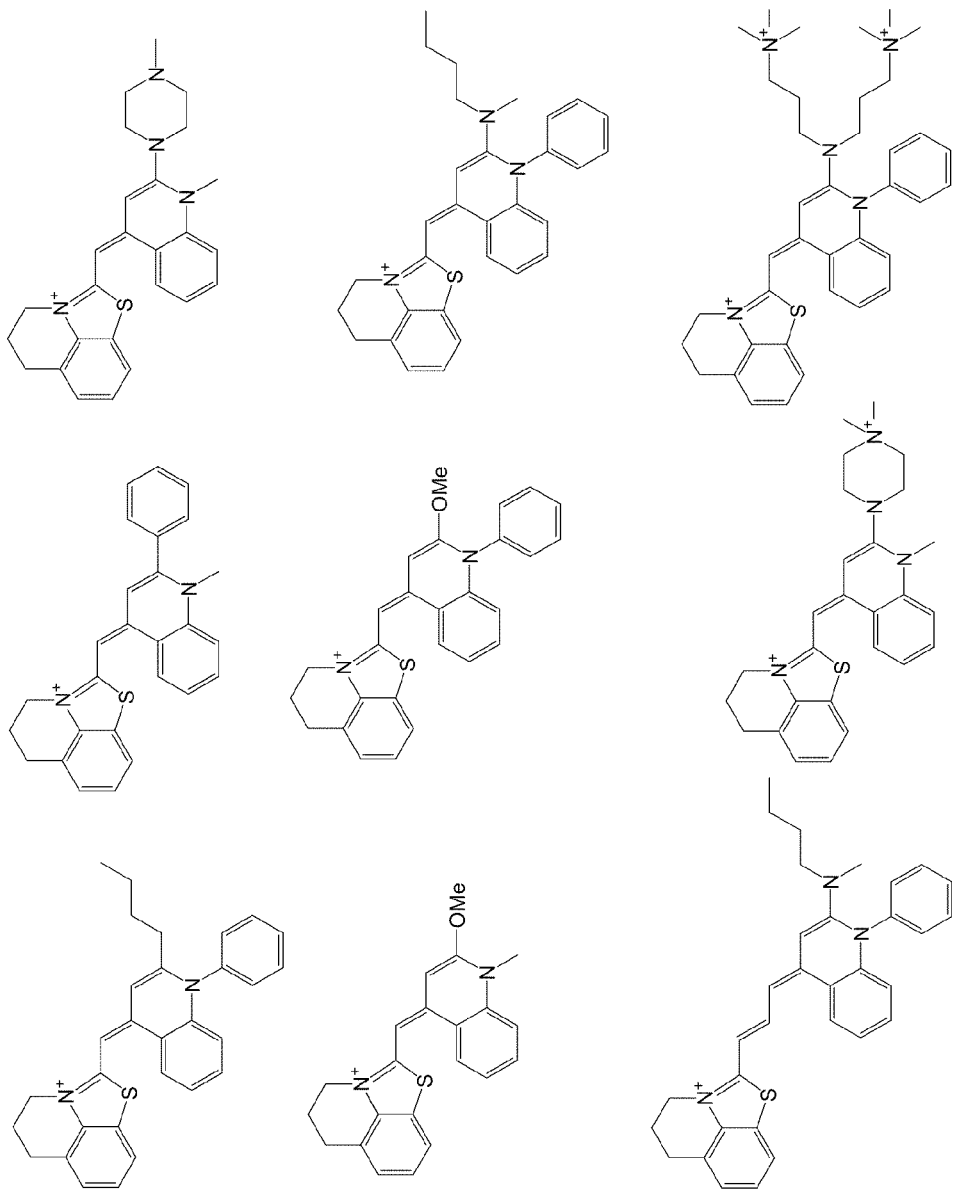
FIG. 6. Structures of various dyes according to the present invention.

As used herein, the following terms and expressions have the indicated meanings. Specific values listed below for radicals, substituents, and ranges are for illustration only. They do not exclude other defined values or other values within defined ranges for the radicals and substituents.

When a group or moiety can be substituted, the term "substituted" indicates that one or more (e.g., 1, 2, 3, 4, 5, or 6; in some embodiments 1, 2, or 3; and in other embodiments 1 or 2) hydrogens on the group indicated in the expression using "substituted" can be replaced with a selection of recited indicated groups or with a suitable group known to those of skill in the art (e.g., one or more of the groups recited below), provided that the indicated atom's normal valency is not exceeded, and that the substitution results in a stable compound. Suitable substituents of a substituted group can include alkyl, alkenyl, alkynyl, alkoxy, halo, haloalkyl, hydroxy, hydroxyalkyl, aryl, heteroaryl, heterocycle, cycloalkyl, alkanoyl, alkoxycarbonyl, amino, alkylamino, dialkylamino, trifluoromethylthio, difluoromethyl, acetylamino, nitro, trifluoromethyl, trifluoromethoxy, carboxy, carboxyalkyl, keto, thioxo, alkylthio, alkylsulfinyl, alkylsulfonyl, arylsulfinyl, arylsulfonyl, heteroarylsulfinyl, heteroarylsulfonyl, heterocyclesulfinyl, heterocyclesulfonyl, phosphate, sulfate, hydroxylamine, hydroxyl (alkyl)amine, and cyano. Additionally, the suitable indicated groups can include, e.g., —X, —R, —O⁻, —OR, —SR, —S⁻, —NR₂, —NR₃, =NR, —CX₃, —CN, —OCN, —SCN, —N=C=O, —NCS, —NO, —NO₂, =N₂, —N₃, NC(=O)R, —C(=O)R, —C(=O)NRR—S(=O)₂O⁻, —S(=O)₂OH, —S(=O)₂R, —OS(=O)₂OR, —S(=O)₂NR, —S(=O)R, —OP(=O)O₂RR, —P(=O)O₂RR, —P(=O)(O⁻)₂, —P(=O)(OH)₂, —C(=O)R, —C(=O)X, —C(S)R, —C(O)OR, —C(O)O⁻, —C(S)OR, —C(O)SR, —C(S)SR, —C(O)NRR, —C(S)NRR, —C(NR)NRR, where each X is independently a halogen ("halo"): F, Cl, Br, or I; and each R is independently H, alkyl, aryl, heteroaryl, heterocycle, a protecting group or prodrug moiety. As would be readily understood by one skilled in the art, when a substituent is keto (=O) or thioxo (=S), or the like, then two hydrogen atoms on the substituted atom are replaced.

As used herein, the term "alkyl" refers to a branched, unbranched, or cyclic hydrocarbon having, for example, from 1 to 20 carbon atoms, and often 1 to 12, or 1 to about 6 carbon atoms. Examples include, but are not limited to, methyl, ethyl, 1-propyl, 2-propyl, 1-butyl, 2-methyl-1-propyl, 2-butyl, 2-methyl-2-propyl (t-butyl), 1-pentyl, 2-pentyl, 3-pentyl, 2-methyl-2-butyl, 3-methyl-2-butyl, 3-methyl-1-butyl, 2-methyl-1-butyl, 1-hexyl, 2-hexyl, 3-hexyl, 2-methyl-2-pentyl, 3-methyl-2-pentyl, 4-methyl-2-pentyl, 3-methyl-3-pentyl, 2-methyl-3-pentyl, 2,3-dimethyl-2-butyl, 3,3-dimethyl-2-butyl, hexyl, octyl, decyl, dodecyl, and the like. The alkyl can be unsubstituted or substituted. For example, a substituted alkyl group can be a haloalkyl group, as described below. The alkyl can also be optionally partially or fully unsaturated. As such, the recitation of an alkyl group includes both alkenyl and alkynyl groups. The alkyl can be a monovalent hydrocarbon radical, as described and exemplified above, or it can be a divalent hydrocarbon radical (i.e., alkylene), according to the context of its usage. Additionally, the alkyl group can be optionally interrupted, as described below for the term interrupted.

The term "alkenyl" refers to a monoradical branched or unbranched partially unsaturated hydrocarbon chain (i.e. a carbon-carbon, $sp^2$ double bond). In one embodiment, an alkenyl group can have from 2 to 10 carbon atoms, or 2 to 6 carbon atoms. In another embodiment, the alkenyl group has from 2 to 4 carbon atoms. Examples include, but are not limited to, ethylene or vinyl, allyl, cyclopentenyl, 5-hexenyl, and the like. The alkenyl can be unsubstituted or substituted.

The term "alkynyl" refers to a monoradical branched or unbranched hydrocarbon chain, having a point of complete unsaturation (i.e. a carbon-carbon, sp triple bond). In one embodiment, the alkynyl group can have from 2 to 10 carbon atoms, or 2 to 6 carbon atoms. In another embodiment, the alkynyl group can have from 2 to 4 carbon atoms. This term is exemplified by groups such as ethynyl, 1-propynyl, 2-propynyl, 1-butynyl, 2-butynyl, 3-butynyl, 1-hexynyl, 2-hexynyl, 3-hexynyl, 1-octynyl, and the like. The alkynyl can be unsubstituted or substituted.

The term "cycloalkyl" refers to cyclic alkyl groups of from 3 to about 10 carbon atoms having a single cyclic ring or multiple condensed rings. Such cycloalkyl groups include, by way of example, single ring structures such as cyclopropyl, cyclobutyl, cyclopentyl, cyclooctyl, and the like, or multiple ring structures such as adamantanyl, and the like. The cycloalkyl can be unsubstituted or substituted. The cycloalkyl group can be monovalent or divalent, and can be optionally substituted as described above for alkyl groups. The cycloalkyl group can optionally include one or more cites of unsaturation, for example, the cycloalkyl group can include one or more carbon-carbon double bonds, such as, for example, cyclohexene, 1,3-cyclohexadiene, 1,4-cyclohexadiene, and the like. The cycloalkyl group can be a carbocycle, which refers to a saturated or partially unsaturated ring having 3 to 8 carbon atoms as a monocycle, 7 to 12 carbon atoms as a bicycle, and up to about 20 carbon atoms as a polycycle. Monocyclic carbocycles typically have 3 to 6 ring atoms, still more typically 5 or 6 ring atoms. Bicyclic carbocycles have 7 to 12 ring atoms, e.g., arranged as a bicyclo [4,5], [5,5], [5,6] or [6,6] system, or 9 or 10 ring atoms arranged as a bicyclo [5,6] or [6,6] system. Examples of carbocycles include cyclopropyl, cyclobutyl, cyclopentyl, 1-cyclopent-1-enyl, 1-cyclopent-2-enyl, 1-cyclopent-3-enyl, cyclohexyl, 1-cyclohex-1-enyl, 1-cyclohex-2-enyl, or 1-cyclohex-3-enyl. The carbocycle can be optionally substituted as described above for alkyl groups.

The term "alkoxy" refers to the group alkyl-O—, where alkyl is as defined herein. In one embodiment, alkoxy groups include, e.g., methoxy, ethoxy, n-propoxy, iso-propoxy, n-butoxy, tert-butoxy, sec-butoxy, n-pentoxy, n-hexyloxy, 1,2-dimethylbutoxy, and the like. The alkoxy can be unsubstituted or substituted.

The term "aryl" refers to an aromatic hydrocarbon group derived from the removal of one hydrogen atom from a single carbon atom of a parent aromatic ring system. The radical can be at a saturated or unsaturated carbon atom of the parent ring system. The aryl group can have 6-18 carbon atoms, 6-14 carbon atoms, or 6-10 carbon atoms. The aryl group can have a single ring (e.g., phenyl) or multiple condensed (fused) rings, wherein at least one ring is aromatic (e.g., naphthyl, dihydrophenanthrenyl, fluorenyl, or anthryl). Typical aryl groups include, but are not limited to, radicals derived from benzene, naphthalene, anthracene, biphenyl, and the like. The aryl can be unsubstituted or optionally substituted, as described above for alkyl groups. For example, an aryl group can be substituted with one or more substituents (as described above) to provide various substituted aryls, such as pentafluorophenyl or para-trifluoromethylphenyl, and the like.

The term "halo" refers to the groups fluoro, chloro, bromo, and iodo. Similarly, the term "halogen" refers to fluorine, chlorine, bromine, and iodine.

The term "heteroaryl" is defined herein as a monocyclic, bicyclic, or tricyclic ring system containing one, two, or three aromatic rings and containing at least one nitrogen, oxygen, or sulfur atom in an aromatic ring, and that can be unsubstituted or substituted, for example, with one or more, and in particular one to three, substituents, as described above in the definition of "substituted". Typical heteroaryl groups contain 2-14 carbon atoms in addition to the one or more heteroatoms. Examples of heteroaryl groups include, but are not limited to, 2H-pyrrolyl, 3H-indolyl, 4H-quinolizinyl, acridinyl, benzo [b]thienyl, benzothiazolyl, -carbolinyl, carbazolyl, chromenyl, cinnolinyl, dibenzo[b,d]furanyl, furazanyl, furyl, imidazolyl, imidizolyl, indazolyl, indolisinyl, indolyl, isobenzofuranyl, isoindolyl, isoquinolyl, isothiazolyl, isoxazolyl, naphthyridinyl, oxazolyl, pyrimidinyl, phenanthridinyl, phenanthrolinyl, phenarsazinyl, phenazinyl, phenothiazinyl, phenoxathiinyl, phenoxazinyl, phthalazinyl, pteridinyl, purinyl, pyranyl, pyrazinyl, pyrazolyl, pyridazinyl, pyridyl, pyrimidinyl, pyrimidinyl, pyrrolyl, quinazolinyl, quinolyl, quinoxalinyl, thiadiazolyl, thianthrenyl, thiazolyl, thienyl, triazolyl, tetrazolyl, and xanthenyl. In one embodiment the term "heteroaryl" denotes a monocyclic aromatic ring containing five or six ring atoms containing carbon and 1, 2, 3, or 4 heteroatoms independently selected from non-peroxide oxygen, sulfur, and N(Z) wherein Z is absent or is H, O, alkyl, aryl, or $(C_1-C_6)$alkylaryl. In another embodiment heteroaryl denotes an ortho-fused bicyclic heterocycle of about eight to ten ring atoms derived therefrom, particularly a benz-derivative or one derived by fusing a propylene, trimethylene, or tetramethylene diradical thereto.

The term "heterocycle" refers to a saturated or partially unsaturated ring system, containing at least one heteroatom selected from the group oxygen, nitrogen, and sulfur, with a ring size of 3 to about 12 atoms, or bicyclic ring systems that include a total of about 7 to about 14 ring atoms, and optionally substituted with one or more groups as defined herein under the term "substituted". A heterocycle can be a monocyclic, bicyclic, or tricyclic group containing one or more heteroatoms. A heterocycle group also can contain an oxo group (=O) or a thioxo (=S) group attached to the ring. Non-limiting examples of heterocycle groups include 1,3-dihydrobenzofuran, 1,3-dioxolane, 1,4-dioxane, 1,4-dithiane, 2H-pyran, 2-pyrazoline, 4H-pyran, chromanyl, imidazolidinyl, imidazolinyl, indolinyl, isochromanyl, isoindolinyl, morpholine, piperazinyl, piperidine, piperidyl, pyrazolidine, pyrazolidinyl, pyrazolinyl, pyrrolidine, pyrroline, quinuclidine, and thiomorpholine.

The term "heterocycle" can include, by way of example and not limitation, a monoradical of the heterocycles described in Paquette, Leo A.; *Principles of Modern Heterocyclic Chemistry* (W. A. Benjamin, New York, 1968), particularly Chapters 1, 3, 4, 6, 7, and 9; *The Chemistry of Heterocyclic Compounds, A Series of Monographs*" (John Wiley & Sons, New York, 1950 to present), in particular Volumes 13, 14, 16, 19, and 28; and *J. Am. Chem. Soc.* 1960, 82, 5566. In one embodiment, "heterocycle" includes a "carbocycle" as defined herein, wherein one or more (e.g. 1, 2, 3, or 4) carbon atoms have been replaced with a heteroatom (e.g. O, N, or S).

Heterocycles, by way of example and not limitation, include dihydropyridyl, tetrahydropyridyl (piperidyl), thiazolyl, tetrahydrothiophenyl, sulfur oxidized tetrahydrothiophenyl, pyrimidinyl, furanyl, thienyl, pyrrolyl, pyrazolyl, piperidinyl, 4-piperidonyl, pyrrolidinyl, 2-pyrrolidonyl, pyrrolinyl, tetrahydrofuranyl, tetrahydroquinolinyl, tetrahydroisoquinolinyl, decahydroquinolinyl, octahydroisoquinolinyl, azocinyl, triazinyl, 6H-1,2,5-thiadiazinyl, 2H,6H-1,5,2-dithiazinyl, thienyl, thianthrenyl, pyranyl, isobenzofuranyl, chromenyl, xanthenyl, phenoxathinyl, 2H-pyrrolyl, isothiazolyl, isoxazolyl, pyrazinyl, pyridazinyl, indolizinyl, isoindolyl, 3H-indolyl, 1H-indazoly, purinyl, 4H-quinolizinyl, phthalazinyl, naphthyridinyl, quinoxalinyl, quinazolinyl, cinnolinyl, pteridinyl, carbazolyl, β-carbolinyl, phenanthridinyl, acridinyl, pyrimidinyl, phenanthrolinyl, phenazinyl, phenothiazinyl, furazanyl, phenoxazinyl, isochromanyl, chromanyl, imidazolidinyl, imidazolinyl, pyrazolidinyl, pyrazolinyl, piperazinyl, indolinyl, isoindolinyl, quinuclidinyl, morpholinyl, oxazolidinyl, benzotriazolyl, benzisoxazolyl, oxindolyl, benzoxazolinyl, isatinoyl, and bis-tetrahydrofuranyl.

By way of example and not limitation, carbon bonded heterocycles are bonded at position 2, 3, 4, 5, or 6 of a pyridine, position 3, 4, 5, or 6 of a pyridazine, position 2, 4, 5, or 6 of a pyrimidine, position 2, 3, 5, or 6 of a pyrazine, position 2, 3, 4, or 5 of a furan, tetrahydrofuran, thiofuran, thiophene, pyrrole or tetrahydropyrrole, position 2, 4, or 5 of an oxazole, imidazole or thiazole, position 3, 4, or 5 of an isoxazole, pyrazole, or isothiazole, position 2 or 3 of an aziridine, position 2, 3, or 4 of an azetidine, position 2, 3, 4, 5, 6, 7, or 8 of a quinoline or position 1, 3, 4, 5, 6, 7, or 8 of an isoquinoline. Carbon bonded heterocycles include 2-pyridyl, 3-pyridyl, 4-pyridyl, 5-pyridyl, 6-pyridyl, 3-pyridazinyl, 4-pyridazinyl, 5-pyridazinyl, 6-pyridazinyl, 2-pyrimidinyl, 4-pyrimidinyl, 5-pyrimidinyl, 6-pyrimidinyl, 2-pyrazinyl, 3-pyrazinyl, 5-pyrazinyl, 6-pyrazinyl, 2-thiazolyl, 4-thiazolyl, 5-thiazolyl, and the like.

By way of example and not limitation, nitrogen bonded heterocycles can be bonded at position 1 of an aziridine, azetidine, pyrrole, pyrrolidine, 2-pyrroline, 3-pyrroline, imidazole, imidazolidine, 2-imidazoline, 3-imidazoline, pyrazole, pyrazoline, 2-pyrazoline, 3-pyrazoline, piperidine, piperazine, indole, indoline, 1H-indazole, position 2 of a isoindole, or isoindoline, position 4 of a morpholine, and position 9 of a carbazole, or β-carboline. In one embodiment, nitrogen bonded heterocycles include 1-aziridyl, 1-azetedyl, 1-pyrrolyl, 1-imidazolyl, 1-pyrazolyl, and 1-piperidinyl.

The term "amino" refers to $-NH_2$. The amino group can be optionally substituted as defined herein for the term "substituted", e.g., the amino group can be $-NR_2$ where R is a group recited in the definition of substituted. For example, the groups $-NR_2$ can include "alkylamino" wherein at least one R is alkyl and the second R is alkyl or hydrogen, and/or "acylamino" ($-N(R)C(=O)R$), wherein each R is independently hydrogen, alkyl, alkaryl or aryl.

The term "alkaryl" refers to an aryl group substituted with at least one alkyl group, which together form a substituent through a radical on either the alkyl or the aryl group. The alkyl group of the alkaryl can include about 1-8 carbon atoms, either linear or branched. Typical alkaryl groups include benzyl, 2-phenylethyl, 3-phenylpropyl, 4-phenylbuty, 5-phenylpentyl, 6-phenylhexyl, 7-phenylheptyl, 8-phenyloctyl, branched alkyl chain derivatives thereof, and naphthalene versions thereof. The alkaryl can be optionally substituted as described above for alkyl groups.

The term "interrupted" indicates that another group is inserted between two adjacent carbon atoms (and the hydrogen atoms to which they are attached (e.g., methyl ($CH_3$), methylene ($CH_2$) or methine (CH))) of a particular carbon chain being referred to in the expression using the term "interrupted", provided that each of the indicated atoms' normal valency is not exceeded and the interruption results in a stable compound. Suitable groups that can interrupt a carbon chain include, e.g., with one or more non-peroxide oxy ($-O-$), thio ($-S-$), imino ($-N(H)-$), methylene dioxy ($-OCH_2O-$), carbonyl ($-C(=O)-$), carboxy ($-C(=O)O-$), carbonyldioxy ($-OC(=O)O-$), carboxylato ($-OC(=O)-$), imine ($C=NH$), sulfinyl (SO) and sulfonyl ($SO_2$). Alkyl groups can be interrupted by one or more (e.g., 1, 2, 3, 4, 5, or about 6) of the aforementioned suitable groups. The site of interruption can also be between a carbon atom of an alkyl group and a carbon atom to which the alkyl group is attached.

As to any of the above groups, which contain one or more substituents, it is understood, of course, that such groups do not contain any substitution or substitution patterns that are sterically impractical and/or synthetically non-feasible. In addition, the compounds of this invention include all stereochemical isomers arising from the substitution of these compounds.

As used herein, "low background" of a dye includes low emission fluorescence at the detection wavelength in the absence of nucleic acids and/or in the presence of other macromolecules, such as those in a complex reaction mixture, including but not limited to proteins and other biomolecules, and the dye itself (i.e., a mixture that lacks a nucleic acid). Thus, the low background is the fluorescence in the presence of the dye but in the absence of nucleic acids.

As used herein, a "bright" dye includes one with a maximum change of fluorescence (without consideration of a normalization, e.g., to 5-carboxy-x-rhodamine (ROX)). For instance, a dye of the invention may be as bright or brighter than SG.

As used herein, "$F_i$" means the initial background fluorescence at cycle 1 in a nucleic acid amplification reaction, for all reactions including the no target reaction, i.e., no template control (NTC) (dye fluorescence in the absence of nucleic acids but in the presence of single stranded oligonucleotides, stabilizing proteins, enzyme, antibodies, and the like, which form part of the initial reaction mixture) and Δ[Target nucleic acid] compositions.

As used herein, "$F_M$" means the maximum fluorescence in all Atarget reactions and the NTC reaction at cycle 45, e.g., the maximum level of fluorescent change in amplification reactions at 45 cycles with 100 ng of target nucleic acid, either viewed as the maximum of the un-normalized amplification curve, or as the maximum fluorescent signal recorded in the 100 ng reactions in the spectral view of the data.

As used herein, "ΔR" means the total change of fluorescence over 45 cycles in amplification curves with baseline subtraction, e.g., default AB 7500 baseline subtraction.

As used herein, "high contrast" brightness is relative to background, i.e., light is known by dark. The detection of brightness is impacted by the inherent background of the system.

As used herein, "$B_{ds}$" means brightness factor=ratio of $F_M:F_i$ (NTC). The brightness of each dye in the formulation is expressed as a ratio of the maximum fluorescence and the no target starting point. Its inverse, $F_B$ (background fluorescence factor), is a factor reflects the ratio of the starting fluorescence in the absence of target to the maximum seen in the primer/target amplification. $F_B$ thus reflects the relative proportion of the starting level of fluorescence to the potential maximum level.

As used herein, a "sensitive" dye includes one which is sensitive in a qPCR reaction, for instance, where the fluorescence of the dye binding to a low concentration of target nucleic acid, such as that found in the 100 ng reactions, is evident over the background of the NTC reaction.

As used herein, an "efficient" amplification reaction includes a nucleic acid specific dye and a control dye, e.g., ROX, for normalization, that results in a standard curve slope of about −3.3 (a slope ≥3.40 is likely indicative of inhibition).

As used herein, "linear" with respect to the dynamic range of a nucleic acid amplification reaction assay includes a standard curve $R^2$ of about 0.99.

Dye Structure

The invention therefore provides a compound or dye of Formula I

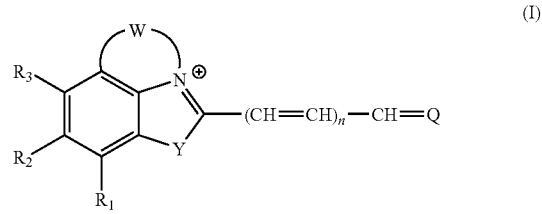

(I)

wherein
$R^1$, $R^2$ and $R^3$ are each independently H, alkyl, cycloalkyl, aryl, heteroaryl, amino, hydroxy, or halo; or $R^1$ and $R^2$, or $R^2$ and $R^3$, taken together with the atoms to which they are attached form a fused benzo ring that is optionally substituted with 1, 2, 3, or 4 alkyl, cycloalkyl, aryl, heteroaryl, amino, hydroxy, or halo groups;

Y is S, O, $CF_2$, or $NR^4$;
$R^4$ is $(C_1-C_8)$alkyl, aryl, or $(C_1-C_8)$alkaryl;
W taken together with the atoms to which it is attached is a 5-, 6-, 7-, or 8-membered heterocyclic ring;
n is 0, 1, or 2;
Q is Q1 or Q2:

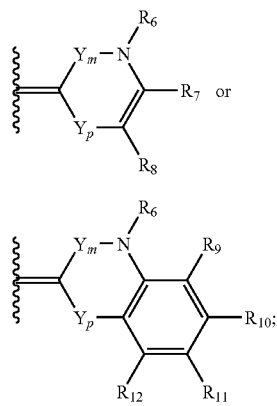

wherein
Y is $-CR^{13}=CR^{14}-$; m and p are 0 or 1 such that m+p=1;
$R^6$ is $(C_1-C_8)$alkyl, aryl, or $(C_1-C_8)$alkaryl;
$R^7$, $R^8$, $R^9$, $R^{10}$, $R^{11}$, and $R^{12}$ are each independently H, alkyl, cycloalkyl, aryl, heteroaryl, amino, or halo;
one of $R^{13}$ and $R^{14}$ is H and the other is $NR^{15}R^{16}$;
$R^{15}$ is $(C_1-C_6)$alkyl or $(C_1-C_6)$alkyl-$NR^{17}R^{18}$, wherein $R^{17}$ and $R^{18}$ are each independently H or $(C_1-C_6)$alkyl; and
$R^{16}$ is $(C_6)$alkyl-$NR^{17}R^{18}$, wherein $R^{17}$ and $R^{18}$ are each independently H or $(C_1-C_6)$alkyl;
or a salt thereof.

In some embodiments, $R^1$, $R^2$ and $R^3$ are each H. In other embodiments, $R^1$, $R^2$ and $R^3$ are each independently H, alkyl, cycloalkyl, aryl, heteroaryl, amino, hydroxy, or halo. In some embodiments, $R^1$ and $R^2$, taken together with the atoms to which they are attached form a fused benzo ring. In other embodiments, $R^2$ and $R^3$, taken together with the atoms to which they are attached form a fused benzo ring.

In some embodiments, Y is S. In other embodiments, Y is O, $CF_2$, or $NR^4$. $R^4$ can be $(C_1-C_8)$alkyl, such as methyl, ethyl, propyl, butyl, pentyl, hexyl, heptyl, octyl, or branched isomers thereof; aryl, such as phenyl or naphthyl; or $(C_1-C_8)$alkaryl, such as benzyl, 2-phenylethyl, or 3-phenylpropyl. In one specific embodiment, Y is S; and n is 0. The value of n can also be 1, or 2. In some embodiments, W taken together with the atoms to which it is attached is a 6-membered heterocyclic ring.

In some embodiments, Q is Q1; in other embodiments, Q is Q2. In one embodiment, Q is Q1; m is 1; $R^6$ is methyl, ethyl, propyl, phenyl, benzyl, 2-phenylethyl, or 3-phenylpropyl; $R^7$ and $R^8$ are both H; $R^{13}$ is H; $R^{14}$ is $NR^{15}R^{16}$ wherein $R^{15}$ is methyl, ethyl, propyl, or butyl. In another embodiment, Q is Q2; m is 1; $R^6$ is methyl, ethyl, propyl, phenyl, benzyl, 2-phenylethyl, or 3-phenylpropyl; $R^9$, $R^{10}$, $R^{11}$, and $R^{12}$ are each H; $R^{13}$ is H; $R^{14}$ is $NR^{15}R^{16}$ wherein $R^{15}$ is methyl, ethyl, propyl, or butyl. In any preceding embodiment, $R^{16}$ can be, for example, $(C_1-C_3)$alkyl-$N(Me)_2$. In some embodiments, $R^{14}$ can be

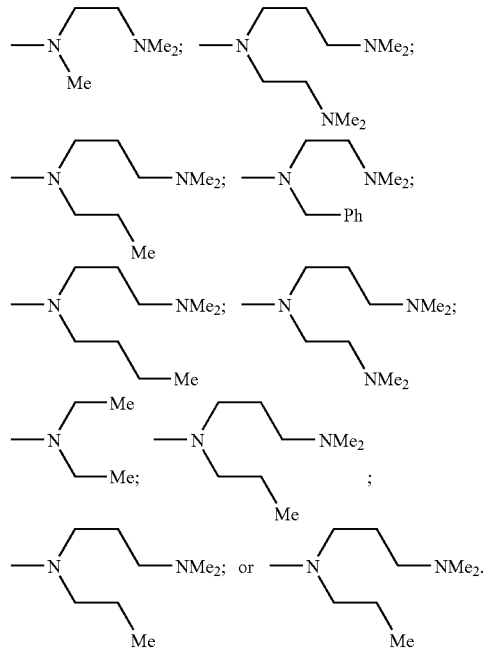

In some embodiments, the compound of formula I is a compound of formula II:

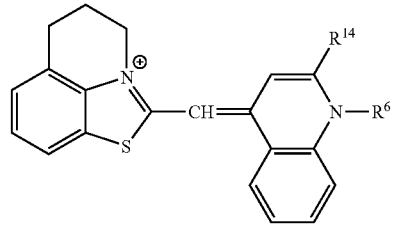

wherein $R^6$ and $R^{14}$ are as defined above. In some embodiments, $R^6$ is methyl, ethyl, propyl, phenyl, benzyl, 2-phenylethyl, or 3-phenylpropyl, and $R^{14}$ is as defined above. The dyes of the invention can display enhanced emission in the presence of nucleic acids, in either in vitro or in vivo environments, for example, compared to its emission in the same environment lacking nucleic acids.

Certain embodiments are shown in FIG. 6.

Each of the dyes of the invention includes at least one positively charged nitrogen atom in the polycyclic core. One skilled in the art will readily recognize that the dyes of the invention also include resonance forms of formulas I and II, where electrons of the conjugated system are rearranged such that the positively charged nitrogen can be found on the alternate nitrogen (i.e., on the nitrogen of $R^6$). Certain of the dyes can be used as impermeant cellular probes, whereas others can be used as permeant cellular probes.

Synthesis

A useful synthetic route to the dyes of the present invention can be described in three parts, following the natural breakdown in the description of the compounds. In general, the synthesis of these dyes requires three precursors: a benzazolium salt, a pyridinium (or quinolinium) salt (both of which have the appropriate chemical substituents, or can be converted to a structure with the appropriate substituents), and (where n=1 or 2) a source for the methine spacer. The synthetic steps that are required to prepare and combine these precursors so as to yield any of the subject derivatives is generally well-understood by one skilled in the art. Although there are many possible variations that may yield an equivalent result, provided herein are some useful general methods for their synthesis and incorporation of chemical modifications.

The Benzazolium Moiety

A wide variety of derivatives of this type for use in preparing photographic dyes have been described, in particular by Brooker and colleagues (Brooker et al., *J. Am. Chem. Soc.*, 64:199 (1942). If Y is O, the precursor compound is a benzoxazolium; if Y is S it is a benzothiazolium; if Y is Se it is a benzoselenazolium; if Y is N or an alkyl substituted N it is a benzimidazolium; and if Y is $CR^{16}R^{17}$ (where $R^{16}$ and $R^{17}$ are, for example, independently H, F, or $(C_1-C_6)$alkyl) then it is an indolinium derivative. Commonly $R^{16}$ and $R^{17}$ are both F or both methyl. Compounds where Y is O or S are widely commercially available from suppliers such as Acros and Sigma-Aldrich. The ring W can be formed by the cyclization of an appropriately functionalized parent benzazole or alternatively prepared from an optionally substituted tetrahydroquinoline by following the procedures outlines in the Examples below.

Groups $R^1$, $R^2$, and $R^3$ are typically incorporated in the parent benzazole or tetrahydroquinoline molecule prior to quaternization, for example, with an alkylating agent. The counterion of the quaternized nitrogen can be an ion Z where Z frequently becomes the counterion on the resultant dye. The counterion may be exchanged for another counterion by methods known in the art, such as the use of ion exchange resins or by precipitation. Examples of Z include but are not limited to halo, such as iodide, bromide, or chloride; sulfate; p-toluenesulfonate; and trifluoromethanesulfonate.

The spacer group is formed from a substituent whose nature is determined by the synthetic method utilized to couple the benzazolium precursor with the pyridinium or quinolinium precursor. When n=0, the spacer group is usually formed from alkylthio, commonly methylthio, or the spacer group is chloro, bromo or iodo. When n=1 or 2, the spacer group can be methyl. Only in the case of where the spacer group is methyl is any part of the spacer group incorporated in the final compound.

The Pyridinium or Quinolinium Moiety

The strongly conjugated ring system of the compounds described herein allows resonance stabilization of the single positive charge on the ring atoms to be distributed over the entire molecule. In particular, the charge is stabilized by partial localization on each of the heterocyclic nitrogen atoms of the dye. As the subject dye is drawn herein, the positive charge is formally localized on the benzazolium portion of the dye. However, it is commonly understood that a comparable resonance structure can be drawn in which the positive charge is formally localized on the pyridinium portion of the dye. Consequently, this latter portion of the molecule can be referred to as a pyridine, pyridinium, quinoline or quinolinium moiety, although in the resonance structure shown, it would formally be termed a dihydropyridine or dihydroquinoline.

Compounds containing the quinolinium moiety in this invention differ from those that contain a single pyridinium ring only in the presence of an additional aromatic ring containing four carbon atoms that is fused at the $R^7$ and $R^8$ positions of the parent structure. Except where reference is to a specific pyridine or pyridinium salt, it is understood that mention of pyridines or pyridinium salts encompasses benzopyridines and benzopyridinium salts, which are formally called quinolines or quinolinium salts. Mention of quinolines and quinolinium salts refer only to structures containing two fused aromatic rings.

In the synthesis of the dyes of the invention, the second heterocyclic precursor is usually a pyridinium salt that is already appropriately substituted. Alternatively, substituents can be incorporated into the pyridinium structure subsequent to attachment of the benzazolium portion of the dye.

Aside from the structural differences between pyridines and quinolines, there exist two major structural distinctions within the family of dyes described in the invention, related to the point of attachment of the pyridinium moiety. In one case (where m is 0 and p is 1) the position of attachment places the methine bridge adjacent to the ring nitrogen (2-pyridines). In other embodiments (where m is 1 and p is 0) the position of the nitrogen atom is para to the point of attachment (4-pyridines).

When n is 0, the group to be coupled to the spacer is methyl, chloro, bromo, or iodo. When n is 1 or 2, the group to be coupled to the spacer is methyl. Only when n is 1 or n is 2 is any part of the group to be coupled to the spacer incorporated in the final compound.

There are several general methods for the synthesis of derivatives of pyridinium, including those derivatives having substituents at any available position, including substitutions that are or that can be converted to before or after reaction with the benzazolium portion to form the dye core structure. Substitutions at $R^6$ or at the position immediately adjacent to the nitrogen atom to which $R^6$ is attached (i.e., at $R^{14}$ when m is 1 and p is 0) are particularly important.

Method 1. Alkylation of the nitrogen atom of an appropriately substituted quinoline with an alkylating agent such as a primary aliphatic halide, sulfate ester, sulfonate ester, epoxide or similar reagent directly yields a substituted quinolinium salt. For example, treatment of a quinoline with 1,3-diiodopropane and base, followed by heating with trimethylamine, yields a substituent at $R^6$. If there is a substituent, or a group that can be converted to a substituent, at a position other than $R^6$, then simple alkylating agents such as methyl iodide or dimethyl sulfate suffice to add the $R^6$ substituent, where $R^6$ is alkyl.

Method 2. $R^6$ substituents that are aryl or heteroaryl are best incorporated by an Ullmann reaction of aniline or a substituted aniline or of a pyridone or quinolone derivative. In this method, a diaryl amine or aryl-heteroaryl amine (generally commercially available) is condensed with diketene and acid to yield a 4-methyl-N-arylquinolone or a 4-methyl-N-heteroarylquinolone.

In the above formula, aryl can be any aromatic or heteroaromatic ring system. Further, $R^7$, $R^8$, $R^9$, $R^{10}$, $R^{11}$, and $R^{12}$ may be hydrogen, or alkyl, cycloalkyl, aryl, heteroaryl, amino, or halo.

In some embodiments, the 4-methyl-2-quinolone can then be converted to the desired 4-methyl-2-substituted-quinolinium salt by reaction with an organometallic reagent such as a Grignard or organolithium reagent. An $R^{14}$ substituent attached in this way may be, for example, aromatic or aliphatic. Pyridone and quinolone precursors may also be prepared by an Ullmann reaction of the appropriately substituted precursor if the nitrogen atom is hydrogen-substituted. While a variety of 4-methyl-2-quinolones are commercially available, desired derivatives can be synthesized by reaction of aniline or a substituted-aniline with an acetoacetate or acetoacetate equivalent reagent such as diketene.

Pyridone and quinolone intermediates containing a non-hydrogen group at $R^6$ are particularly useful precursors to a wide variety of other pyridinium and quinolinium salts that are substituted at $R^{14}$. For example, a salt can be formed by treatment of the appropriate pyridone or quinolone with a strong chlorinating agent such as $PCl_5$, $POCl_3$ or $SOCl_2$. Similarly, a sulfonate can be substituted at $R^{14}$ by treating the pyridone or quinolone with the appropriate sulfonic acid anhydride.

Halogen Displacement

The reactivity of the 2-halogenated pyridinium or quinolinium intermediate offers a variety of synthetic methods for attachment of various substituents at the 2-position. The reactivity of the 2-halo derivatives is preserved even after conjugation with the benzazolium precursor, enabling conversion of the resulting dye in which $R^{14}$ is halogen into the appropriate analog (including but not limited to alkoxy, amino and thiolate analogs), as described for the pyridinium and quinolinium precursors. The dyes described herein with a 2-chloro substituent may be displaced by, for example, amines, thiols or alcohols. Additionally, the 2-oxo group of pyridone or quinolone precursors can be chemically reduced to derivatives in which $R^{14}$ is H using a variety of reagents including DIBAL-H (diisobutylaluminum hydride).

The Methine Bridge

The methine bridge consists of 1, 3 or 5 methine (—CH=) groups that bridge the benzazolium portion of the molecule and the pyridinium portion in such a way as to permit extensive electronic conjugation. The number of methine groups is determined by the specific synthetic reagents used in the synthesis.

When n is 0, the synthesis of monomethine dyes commonly uses a combination of reagents where the methine carbon atom results from either the spacer group precursor on the benzazolium salt or the group to be coupled to the spacer on the pyridinium salt being methyl and the other being a reactive "leaving group" that is typically methylthio or chloro, but which can be any leaving group that provides sufficient reactivity to complete the reaction. This type of reaction to make unsymmetrical monomethine dyes from two quaternary salts was originally described by Brooker et al., supra. Whether the spacer group precursor or the group to be coupled to the spacer on the pyridinium is methyl depends primarily on the relative ease of synthesis of the requisite precursor salts. Because the compounds described herein typically contain the greatest variation on the pyridinium portion of the molecule; and furthermore, because 2-methyl and 4-methyl pyridines are usually easier to prepare than their corresponding methylthio analogs, the monomethine dyes from precursors in which the spacer group precursor methylthio and the group to be coupled to the spacer group is methyl have typically been prepared. The condensing reagent in the case of monomethine dyes is typically a weak base such as triethylamine or diisopropylethylamine.

To synthesize trimethine dyes (n=1) both the spacer group precursor or the group to be coupled to the spacer on the pyridinium are methyl. In this case the additional methine carbon is provided by a reagent such as diphenylforamidine, N-methyl-formanilide or ethyl orthoformate. Because under certain reaction conditions these same reagents can yield symmetrical cyanine dyes that incorporate two moles of a single quaternary salt, it is often useful to use the proper synthetic conditions, and a suitable ratio of the carbon-providing reactant to the first quaternary salt, so that the proper intermediate will be formed. This intermediate is treated either before or after purification with the second quaternary salt to form the asymmetric cyanine dye. If desired, the counterion Z can be exchanged at this point. Although one can usually react either of the heteroaromatic precursor salts with the carbon-providing reagent to form the required intermediate, the intermediate have been typically formed from the more readily available 2-methylbenzazolium salts as described by Brooker et al., supra.

Synthesis of the pentamethine dyes (n=2) requires the same synthetic concerns about controlling the formation of an asymmetric intermediate. The three-carbon fragment that is required for the additional atoms in the bridge comes from a suitable precursor to malonaldehyde such as malonaldehyde dianil, 1,1,3,3-tetramethoxypropane, 1,1,3-trimethoxypropene, 3-(N-methylanilino)propenal or other reagents. The condensing agent for this reaction is usually 1-anilino-3-phenylimino-1-propene (U.S. Pat. No. 2,269,234), which generates the 2-(2-anilinovinyl)-3-methylbenzazolium tosylate intermediate.

General Methods of Use

In one aspect of the invention, the dye compounds of the invention are used to directly stain or label a sample so that the sample, e.g., a sample having a nucleic acid, e.g. DNA or RNA, can be identified or quantitated. For instance, such dyes may be added as part of an assay for a biological target analyte. In one preferred embodiment, dye conjugate is used to stain a sample that comprises a ligand for which the conjugated substance is a complementary member of a specific binding pair. The sample can be obtained directly from a liquid source or as a wash from a solid material (organic or inorganic) or a growth medium in which cells have been introduced for culturing, or a buffer solution in which cells have been placed for evaluation.

In some embodiments, the sample comprises cells. The cells may be single cells, including microorganisms, or multiple cells associated with other cells in two or three dimensional layers, including multicellular organisms, embryos, tissues, biopsies, filaments, biofilms, etc. The cells may be live cells or dead cells. In some embodiments, the cells are in an animal, i.e. the method is used for in vivo animal imaging.

Alternatively, the sample can be a solid, optionally a smear or scrape or a retentate removed from a liquid or vapor by filtration. In one aspect of the invention, the sample is obtained from a biological fluid, including separated or unfiltered biological fluids such as urine, cerebrospinal fluid, blood, lymph fluids, tissue homogenate, interstitial fluid, cell extracts, mucus, saliva, sputum, stool, physiological secretions or other similar fluids.

In other embodiments, the sample may also be obtained from an environmental source such as soil, water, or air; or from an industrial source such as taken from a waste stream, a water source, a supply line, or a production lot.

In yet another embodiment, the sample is present on or in solid or semi-solid matrix. In one aspect of the invention, the matrix is a membrane. In another aspect, the matrix is an electrophoretic gel, such as is used for separating and characterizing nucleic acids or proteins, or is a blot prepared by transfer from an electrophoretic gel to a membrane. In another aspect, the matrix is a silicon chip or glass slide, and the analyte of interest has been immobilized on the chip or slide in an array (e.g. the sample comprises proteins or nucleic acids in a microarray). In yet another aspect, the matrix is a microwell plate or microfluidic chip, and the sample is analyzed by automated methods, typically by various methods of high-throughput screening, such as drug screening.

The dye compounds of the invention are generally utilized by combining a dye compound of the invention as described above with the sample of interest under conditions selected to yield a detectable optical response. In one embodiment, the dye compound typically forms a non-covalent association or complex with double stranded polynucleotides. The sample is then illuminated at a wavelength selected to elicit the optical response. Typically, staining the sample is used to determine a specified characteristic of the sample by further comparing the optical response with a standard or expected response.

A detectable optical response means a change in, or occurrence of, an optical signal that is detectable either by observation or instrumentally. Typically the detectable response is a change in fluorescence, such as a change in the intensity, excitation or emission wavelength distribution of fluorescence, fluorescence lifetime, fluorescence polarization, or a combination thereof.

For biological applications, the dye compounds of the invention are typically used in an aqueous, mostly aqueous or aqueous-miscible solution prepared according to methods generally known in the art. The exact concentration of dye compound is dependent upon the experimental conditions and the desired results, but typically ranges from about one nanomolar to one millimolar or more. The optimal concentration is determined by systematic variation until satisfactory results with minimal background fluorescence is accomplished.

At any time after or during staining, the sample is illuminated with a wavelength of light selected to give a detectable optical response, and observed with a means for detecting the optical response. Equipment that is useful for illuminating the dye compounds of the invention includes, but is not limited to, hand-held ultraviolet lamps, mercury arc lamps, xenon lamps, lasers and laser diodes. These illumination sources are optionally integrated into laser scanners, fluorescence microplate readers, standard or minifluorometers, or chromatographic detectors.

The optical response is optionally detected by visual inspection, or by use of any of the following devices: CCD cameras, video cameras, photographic film, laser-scanning devices, fluorometers, photodiodes, quantum counters, epifluorescence microscopes, scanning microscopes, flow cytometers, fluorescence microplate readers, or by means for amplifying the signal such as photomultiplier tubes. Where the sample is examined using a flow cytometer, examination of the sample optionally includes sorting portions of the sample according to their fluorescence response.

In one embodiment, the dye of the present invention is combined with a sample that contains or is thought to contain a nucleic acid (polynucleotide) under conditions and for a time sufficient for the dye to combine with the polynucleotide in the sample to form one or more dye-nucleic acid complexes having a detectable fluorescent signal, e.g., one that is different than free dye. The characteristics of the dye-nucleic acid complexes, including the amount, presence, location, intensity, excitation and emission spectra, fluorescence polarization, fluorescence lifetime, and other physical properties of the fluorescent signal, may be used to detect, differentiate, sort, quantitate, and/or analyze aspects or portions of the sample. The dyes of the invention are optionally used in conjunction with one or more additional reagents (e.g., detectably different fluorescent reagents), including dyes of the same class having different spectral properties.

The dyes of the invention may be used to detect double stranded DNA, e.g., in electrophoretic gels, detect single stranded nucleic acids, e.g., in electrophoretic gels, quantify double stranded DNA in solution, quantify single stranded oligonucleotides in solution, detect oligonucleotides in physiological samples, detect DNase activity, detect nucleic acids on a support, counterstain metaphase chromosomes and interphase nuclei, chromosome banding, detect protein/DNA complexes, e.g., in gels, using pre-labeled DNA templates, detect sequence specific DNA binding proteins in cell extracts, prepare and use prelabeled marker DNA, detect ribosomal RNA, e.g., in sucrose gradients, counterstain fixed tissue culture cells, stain cells in tissue, detect and quantify DNA amplification products, detect single strand conformation polymorphisms, determine superhelical state, label DNA for microinjection, label and detect single DNA molecules, quantify cell number, discriminate between RNA, double stranded DNA and single stranded DNA, for instance, using nucleases in combination with other dyes, and discriminate double stranded DNA from RNA and single stranded DNA.

Kits

One aspect of the instant invention is the formulation of kits that facilitate the practice of various assays using any of the dyes of the invention, as described above. The kits of the invention typically comprise a fluorescent dye of the invention, and may also include other reagents such as a nucleotide, oligonucleotide, nucleic acid, peptide, or protein. The kit optionally further comprises one or more buffering agents, typically present as an aqueous solution. The kits of the invention optionally further comprise additional detection reagents, a purification medium for purifying the resulting labeled substance, luminescence standards, enzymes, enzyme inhibitors, organic solvent, or instructions for carrying out an assay of the invention.

Staining Solution

The dye may be prepared for use by dissolving the dye in a staining solution, e.g., an aqueous or aqueous miscible solution that is compatible with the sample and the intended use. For biological samples, where minimal perturbation of cell morphology or physiology is desired, the staining solution is selected accordingly. For solution assays, in one embodiment, the staining solution does not perturb the native conformation of the nucleic acid undergoing evaluation. At pH higher than 8 and lower than 6.5, fluorescence of the dye-nucleic acid complex and stability of the dyes may be reduced. High concentrations of organic solvents, cations, and oxidizing agents also generally reduce fluorescence, as does the ionic detergent sodium dodecyl sulfate (SDS) at concentrations >0.01%. A number of staining solution additives, however, do not interfere with the fluorescence of the dye-nucleic acid complex (e.g., urea up to 8 M; CsCl up to 1 g/mL; formamide up to 50% of the solution; and sucrose up to 40%). The dyes may have greater stability in buffered solutions than in water alone; and agents that reduce the levels of free oxygen radicals, such as β-mercaptoethanol, may contribute to the stability of the dyes.

The staining solution may be made by dissolving the dye directly in an aqueous solvent such as water, a buffer solution, such as buffered saline (e.g., non-phosphate for some viability discrimination applications), a Tris(hydroxymethyl)-aminomethane (TRIS) buffer (e.g., containing EDTA), or a water-miscible organic solvent such as dimethylsulfoxide (DMSO), dimethylformamide (DMF), or a lower alcohol such as methanol or ethanol. The dye may be preliminarily dissolved in an organic solvent (e.g., 100% DMSO) at a concentration of greater than about 100 times that used in the staining solution, then diluted one or more times with an aqueous solvent such as water or buffer, such that the dye is present in an effective amount.

An effective amount of dye is the amount sufficient to give a detectable fluorescence response in combination with nucleic acids. The dye concentration in the solution must be sufficient both to contact the nucleic acids in the sample and to combine with the nucleic acids in an amount sufficient to give a signal, yet too much dye will cause problems with background fluorescence. Typically staining solutions for cellular samples may have a dye concentration greater than 0.1 nM and less than 50 μM, such as greater than 1 nM and less than 10 μM, e.g., between 0.5 and 5 μM. In general, lower concentrations of dyes are required for eukaryotes than for prokaryotes and for dyes with higher sensitivity. Staining solutions for electrophoretic gels typically have a dye concentration of greater than 0.1 μM and less than 10 μM, e.g., about 0.5-2 μM; the same holds true where the dye is added to the gel (pre-cast) before being combined with nucleic acids. Staining solutions for detection and quantitation of free nucleic acids in solution may have a concentration of 0.1 μM to 2 μM. The optimal concentration and composition of the staining solution is determined by the nature of the sample (including physical, biological, biochemical and physiological properties), the nature of the dye-sample interaction (including the transport rate of the dye to the site of the nucleic acids), and the nature of the analysis being performed, and can be determined according to standard procedures such as those described in examples below.

Sample Types

The dye may be combined with a sample that contains or is thought to contain a nucleic acid. The nucleic acid in the sample may be RNA or DNA, or a mixture or a hybrid thereof. Any DNA is optionally single-, double-, triple-, or quadruple-stranded DNA. Any RNA is optionally single stranded ("ss") or double stranded ("ds"). The nucleic acid may be natural (biological in origin) or synthetic (modified or prepared artificially). The nucleic acid (e.g., containing at least 8 bases or base pairs) may be present as nucleic acid fragments, oligonucleotides, or larger nucleic acids with secondary or tertiary structure. The nucleic acid may be present in a condensed phase, such as a chromosome. The nucleic acid may optionally contain one or more modified bases or links or contains labels that are non-covalently or covalently attached. For example, the modified base can be a naturally occurring modified base such as pseudouridine in tRNA, 5-methylcytosine, 6-methylaminopurine, 6-dimethylaminopurine, 1-methylguanine, 2-methylamino-6-hydroxypurine, 2-dimethylamino-6-hydroxypurine, or other known minor bases or is synthetically altered to contain an unusual linker such as morpholine derivatized phosphates (AntiVirals, Inc., Corvallis, Oreg.), or peptide nucleic acids such as N-(2-aminoethyl) glycine units (Wittung et al., *Nature*, 368:561 (1994)) or contain a simple reactive functional group (<10 carbons) that is an aliphatic amine, carboxylic acid, alcohol, thiol or hydrazine, or contain a fluorescent label or other hapten, such as inosine, bromodeoxyuridine, iododeoxyuridine, biotin, digoxigenin, 2,4-dinitrophenyl, where the label is originally attached on the nucleotide or on the 3' or 5' end of the polymer, or ligands non-covalently attached to the nucleic acids. The sensitivity of the dyes for polymers containing primarily modified bases and links may be diminished by interference with the binding mode.

A sample that contains the nucleic acid is optionally a biological structure (i.e., an organism or a discrete unit of an organism), or a solution (including solutions that contain biological structures), or a solid or semi-solid material. Consequently, the nucleic acid used to practice the invention is optionally free in solution, immobilized in or on a solid or semi-solid material, extracted from a biological structure (e.g., from lysed cells, tissues, organisms or organelles), or remains enclosed within a biological structure. In order for the nucleic acids to bind to the dyes, it is necessary that the nucleic acids be in an aqueous environment to contact the dye, even if the nucleic acids are not enclosed in a biological structure.

The biological structure that encloses the nucleic acid is optionally a cell or tissue, for example, the nucleic acid may be present in a cell or interstitial space, in a prokaryote or eukaryote microorganism, or as a virus, viroid, chromosome or organelle, or as a cellular component removed from its parent cell (e.g., a plasmid or chromosome, or a mitochondrion or nucleus or other organelle). Typically, the biological structure is an organelle, chromosome or cell that is optionally inside a eukaryote cell. The source of nucleic acid that is present inside a eukaryote cell may be that of a parasite or other infective agent such as a bacterium, protozoa, mycoplasma or mycobacterium. Where the nucleic acid is contained in a biological structure that is a cell, the cells may be viable or dead cells or a mixture thereof, i.e., the integrity of the cell membrane is optionally intact or disrupted by natural (autolytic), mechanical or chemical means or by environmental means such as changes in temperature or pressure. Alternatively, the cells may be blebbing or undergoing apoptosis or in a cycle of growth or cell division.

Cell types for which the dye is an effective nucleic acid stain include cells with or without nuclei, including but not limited to, eukaryotes, such as plant and animal cells (particularly vertebrate cells), including pollen and gamete cells; prokaryotes, particularly bacteria, including both Gram-negative and Gram-positive bacteria as well as yeast and other fungi, and spores. The dyes are not equally effective in staining all cell types and certain dyes are generally more permeant than others. Live cells are less permeable to the dyes than dead cells, and prokaryotes are less permeable than eukaryotes.

The nucleic acids in the sample, both natural and synthetic, may be obtained from a wide variety of sources. The presence of the nucleic acid in the sample may be due to natural biological processes, or the result of successful or unsuccessful synthesis or experimental methodology, undesirable contamination, or a disease state. The nucleic acid may be endogenous to the natural source or introduced as foreign material, such as by infection, transfection, or therapeutic treatment. Nucleic acids may be present in all, or only part, of a sample, and the presence of nucleic acids may be used to distinguish between individual samples, or to differentiate a portion or region within a single sample, or to identify the sample or characteristics of the sample.

In one embodiment, the sample containing nucleic acids is a cell or is an aqueous or aqueous miscible solution that is obtained directly from a liquid source or as a wash from a solid material (organic or inorganic) or a growth medium in which cells have been introduced for culturing or a buffer solution in which nucleic acids or biological structures have been placed for evaluation. Where the nucleic acids are in cells, the cells are optionally single cells, including microorganisms, or multiple cells associated with other cells in two or three dimensional layers, including multicellular organisms, embryos, tissues, biopsies, filaments, biofilms, etc. Alternatively, the sample is a solid, optionally a smear or scrape or a retentate removed from a liquid or vapor by filtration. In one aspect of the invention, the sample is obtained from a biological fluid, including separated or unfiltered biological fluids such as urine, cerebrospinal fluid, blood, lymph fluids, tissue homogenate, interstitial fluid, cell extracts, mucus, saliva, sputum, stool, physiological secretions or other similar fluids. Alternatively, the sample is obtained from an environmental source such as soil, water, or air or from an industrial source such as taken from a waste stream, a water source, a supply line, or a production lot. Industrial sources also include fermentation media, such as from a biological reactor or food fermentation process such as brewing; or foodstuffs, such as meat, gain, produce, or dairy products.

Where the nucleic acid is present in a solution, the sample solution can vary from one of purified or synthetic nucleic acids such as oligonucleotides to crude mixtures such as cell extracts or homogenates or other biological fluids, or dilute solutions from biological, industrial, or environmental sources. In some cases, it is desirable to separate the nucleic acids from a mixture of biomolecules or fluids in the solution prior to combination with the dye. Numerous techniques exist for separation and purification of nucleic acids from generally crude mixtures with other proteins or other biological molecules. These include such means as chromatographic techniques and electrophoretic techniques using a variety of supports or solutions or in a flowing stream. Alternatively, mixtures of nucleic acids may be treated with RNase or DNase so that the polymer that is not degraded in the presence of the nuclease can be discriminated from degradation products using the subject dyes.

The source and type of sample, as well as the use of the dye, may determine which dye characteristics, and thus which dyes, are most useful for staining a particular sample. For most applications, dyes are selected to give a quantum yield greater than about 0.3, e.g., greater than 0.6, when bound to nucleic acid; in one embodiment, the dyes have a quantum yield<0.01 when not bound to nucleic acid, and a fluorescence enhancement of greater than about 200-fold, e.g., greater than 1000-fold. Where the fluorescence of the dye-nucleic acid complex is detected utilizing sustained high intensity illumination (e.g., microscopy), dyes with rate of photobleaching lower than commonly used dyes (e.g., fluorescein) are selected, particularly for use in live cells. The relatively low toxicity of the dyes to living systems generally enables the examination of nucleic acids in living samples with little or no perturbation caused by the dye itself. Where the dye must penetrate cell membranes or a gel, dyes that are more permeant dyes are employed, although some cells readily take up dyes that are shown to be impermeant to other cells by means other than passive diffusion across cell-membranes, e.g., by phagocytosis or other types of ingestion. Dyes that rapidly and readily penetrate cells do not necessarily rapidly penetrate gels. In applications where the nucleic acids are stained on a gel, the dye is also selected to have a high binding affinity (e.g., $K_d>10^{-6}$ M). In applications where the nucleic acid is prestained prior to undergoing a separation step involving electrophoresis, such as in gel or capillary electrophoresis, even higher binding affinity (e.g., $K_d>10^{-8}$ M) may be employed to ensure good separation. In staining nucleic acids in solution, high binding affinity translates into greater sensitivity to small amounts of nucleic acid, but dyes with a moderate binding affinity (preferably $10^{-6}$ M<$K_d$<$10^{-8}$ M) are generally more effective over a greater dynamic range. The photostability, toxicity, binding affinity, quantum yield, and fluorescence enhancement of dyes are determined according to standard methods known in the art.

Formation of Dye-Nucleic Acid Complexes

The sample may be combined with the staining solution by any means that facilitates contact between the dye and the nucleic acid. For example, the contact may occur through simple mixing, as in the case where the sample is a solution. A staining solution containing the dye may be added to the nucleic acid solution directly or may contact the nucleic acid solution in a liquid separation medium such as an electrophoretic liquid, sieving matrix or running buffer, or in a sedimentation (e.g., sucrose) or buoyant density gradient (e.g., containing CsCl), or on an inert matrix such as a blot or gel, a testing strip, or any other solid or semi-solid support. Suitable supports also include, but are not limited to, polymeric microparticles (including paramagnetic microparticles), polyacrylamide and agarose gels, nitrocellulose filters, computer chips (such as silicon chips for photolithography), natural and synthetic membranes, liposomes and alginate hydrogels, and glass (including optical filters), and other silica-based and plastic support. The dye is optionally combined with the nucleic acid solution prior to undergoing gel or capillary electrophoresis, gradient centrifugation, or other separation step, during separation, or after the nucleic acids undergo separation. Alternatively, the dye may be combined with an inert matrix or solution in a capillary prior to addition of the nucleic acid solution, as in pre-cast gels, capillary electrophoresis or preformed density or sedimentation gradients.

Where the nucleic acids are enclosed in a biological structure, the sample may be incubated with the dye. While some permeant dyes permeate biological structures rapidly and completely upon addition of a dye solution, any other technique that is suitable for transporting the dye into the biological structure may be employed to combine the sample with the dye. Some cells actively transport the dyes across cell membranes (e.g., endocytosis or ingestion by an organism or other uptake mechanism) regardless of their cell membrane permeability. Suitable artificial means for transporting the dyes (or pre-formed dye-nucleic acid complexes) across cell membranes include, but are not limited to, action of chemical agents such as detergents, enzymes or adenosine triphosphate; receptor- or transport protein-mediated uptake; liposomes or alginate hydrogels; phagocytosis; pore-forming proteins; microinjection; electroporation; hypoosmotic shock; or minimal physical disruption such as scrape loading, patch clamp methods, or bombardment with solid particles coated with or in the presence of the dyes. In one embodiment, where intact structures are desired, the methods for staining cause minimal disruption of the viability of the cell and integrity of cell or intercellular membranes. Alternatively, the cells may be fixed and treated with routine histochemical or cytochemical procedures, particularly where pathogenic organisms are suspected to be present. The cells may be typically fixed immediately after staining with an aldehyde fixative that keeps the dye in the cells. In some cases, live or dead cells may be fixed prior to staining without substantially increasing cell membrane permeability of previously live cells so that only cells that were dead prior to fixation stain with the cell-impermeant dye.

The sample is combined with the dye for a time sufficient to form the fluorescent nucleic acid-dye complex, such as the minimum time required to give a high signal-to-background ratio. Optimal staining with a particular dye may be dependent upon the physical and chemical nature of the individual sample and the sample medium as well as the property being assessed. The optimal time is usually the minimum time required for the dye, in the concentration being used, to achieve the highest target-specific signal while avoiding degradation of the sample over time and minimizing all other fluorescent signals due to the dye. For example, where the dye is chosen to be selective for a particular nucleic acid or type of cell, the optimal time is usually the minimum time required to achieve the highest signal for that polymer or type of cell, with little to no signal from other nucleic acids or other cell types. Over time, undesirable staining may occur as even very low rates of diffusion transport small amounts of the very sensitive dyes into other cell types, or as the cell membranes degrade, or as nucleases degrade nucleic acids in cell free systems.

In one embodiment, the dye may be combined with the sample at a temperature optimal for biological activity of the nucleic acids within the operating parameters of the dyes (usually between 5° C. and 100° C., with reduced stability of the dyes at even higher temperatures). For in vitro assays, the dye is typically combined with the sample at about room temperature (23° C.). At room temperature, detectable fluorescence in a solution of nucleic acids that form a complex with the dye may be essentially instantaneous depending on the sensitivity of the instrumentation that is used. Fluorescence in solutions is generally visible by eye within 5 seconds after the dye is added, and is generally measurable within 2 to 5 minutes, although reaching equilibrium staining may take longer. Where a biological process is underway during in vitro analysis (e.g., in vitro transcription, replication, splicing, or recombination), the rapid labeling that may occur with the dyes avoids perturbation of biological system that is being observed. Gel staining at room temperature usually takes from 5 minutes to 2 hours depending on the thickness of the gel and the percentage of agarose or polyacrylamide as well as the degree of cross-linking. Typically, post-stained minigels stain to equilibrium in 20-30 minutes. For cells and other biological structures, transport of dyes across membranes may be required whether the membranes are intact or disrupted. In one embodiment, visibly detectable fluorescence is obtained at room temperature within 15-20 minutes of incubation with cells, commonly within about 5 minutes. Some embodiments give detectable fluorescence inside cells in less than about 2 minutes. Some of the dyes are generally not permeant to live cells with intact membranes. Other dyes are generally permeant to eukaryotes but not to prokaryotes. Still other dyes are only permeant to cells in which the cell membrane integrity has been disrupted (e.g., some dead cells). The relative permeability of the cell membrane to the dyes is determined empirically, e.g., by comparison with staining profiles or staining patterns of killed cells. The dye with the desired degree of permeability and a high absorbance and quantum yield when bound to nucleic adds, is selected to be combined with the sample.

Fluorescence of the Dye-Nucleic Acid Complexes

The nucleic acid-dye complex formed during the staining of the sample with a dye of the present invention comprises a nucleic acid non-covalently bound to one or more molecules of dye. The combination of dye and nucleic acid results in a fluorescent signal that is significantly enhanced over the fluorescence of the dye alone. Typically, fluorescence of the dye-nucleic acid complex decreases at pH lower than 6.5 or greater than 8, but can be restored by returning to moderate pH.

The fluorescence dyes of the invention in solution is low, and the absolute degree of enhancement may vary between dyes. The quantum yield of unbound dye is typically <0.01, usually <0.002, and frequently <0.001, which would yield a maximum enhancement of >100×, >500×, and >1000×, respectively. The fold of fluorescence enhancement of the bound dye is generally about 100-1000-fold greater than that of unbound dye, e.g., greater than about 300-fold, such that the dyes have a readily detectable increase in quantum yield upon binding to nucleic acids. The molar absorptivity (extinction coefficient) at the longest wavelength absorption peak of the dyes may be typically >50,000 and frequently >60,000 for the dyes where n=0. Dyes with high extinction coefficients at the excitation wavelength may provide for the highest sensitivity. A useful level of quantum yield and/or other attributes of the dyes, including selectivity for rate of permeation, for binding affinity and/or the selectivity of excitation and emission bands to suit specific instrumentation, make the dyes useful for a very wide range of applications.

The presence, amount, location, and/or distribution of nucleic acid is detected using the spectral properties of the fluorescent dye-nucleic acid complex. Spectral properties means any parameter that may be used to characterize the excitation or emission of the dye-nucleic acid complex including absorption and emission wavelengths, fluorescence polarization, fluorescence lifetime, fluorescence intensity, quantum yield, and fluorescence enhancement. In one embodiment, the spectral properties of excitation and emission wavelength are used to detect the dye-nucleic acid complex. The wavelengths of the excitation and emission bands of the dyes vary with dye composition to encompass a wide range of illumination and detection bands. This allows the selection of individual dyes for use with a specific excitation source or detection filter. In particular, complexes formed with dyes having a monomethine bridge (n=0) generally match their primary excitation band with the commonly used argon laser (488 nm) or HeCd laser (442 nm); whereas those with dyes with a trimethine bridge (n=1) primarily tend to match long wavelength excitation sources such as green HeNe (543 nm), the orange HeNe laser (594 nm), the red HeNe laser (633 nm), mercury arc (546 nm), or the Kr laser (568 or 647 nm); and complexes formed with dyes having a pentamethine bridge (n=2) primarily match very long excitation sources such as laser diodes or light emitting diodes (LEDs). In addition to the primary excitation peak in the visible range, the dye-nucleic acid complexes of the invention may have a secondary absorption peak that permits excitation with UV illumination.

In one embodiment, the sample is excited by a light source capable of producing light at or near the wavelength of maximum absorption of the fluorescent complex, such as an ultraviolet or visible wavelength emission lamp, an arc lamp, a laser, or even sunlight or ordinary room light. In one embodiment, the sample is excited with a wavelength within 20 nm of the maximum absorption of the fluorescent complex. Although excitation by a source more appropriate to the maximum absorption band of the nucleic acid-dye complex results in higher sensitivity, the equipment commonly available for excitation of samples can be used to excite the dyes of the present invention.

The fluorescence of the complex is detected qualitatively or quantitatively by detection of the resultant light emission at a wavelength of greater than about 450 nm, e.g., greater than about 480 nm, such as greater than about 500 nm. Dyes having a quinolinium ring system usually absorb and emit at longer wavelength maxima than similarly substituted dyes having a pyridinium ring system. The emission is detected by means that include visual inspection, CCD cameras, video cameras, photographic film, or the use of current instrumentation such as laser scanning devices, fluorometers, photodiodes, quantum counters, plate readers, epifluorescence microscopes, scanning microscopes, confocal microscopes, flow cytometers, capillary electrophoresis detectors, or by means for amplifying the signal such as a photomultiplier tube. Many such instruments are capable of utilizing the fluorescent signal to sort and quantitate cells or quantitate the nucleic acids. Dyes can be selected to have emission bands that match commercially available filter sets such as that for fluorescein or for detecting multiple fluorophores with several excitation and emission bands.

Use of Complexes

Once the dye-nucleic acid complex is formed, its presence may be detected and used as an indicator of the presence, amount, location, or type of nucleic acids in the sample, as a basis for sorting cells, or as a key to characterizing the sample or cells in the sample. Such characterization may be enhanced by the use of additional reagents, including fluorescent reagents. The nucleic acid concentration in a sample may also be quantified by comparison with known relationships between the fluorescence of the nucleic acid-dye complex and concentration of nucleic acids in the sample.

In one aspect of the invention, the dye-nucleic acid complex may be used as a means for detecting the presence or location of nucleic acids in a sample, where the sample is stained with the dye as described above, and the presence and location of a fluorescent signal indicates the presence of nucleic acids at the corresponding location. The fluorescent signal is detected by eye or by the instrumentation described above. The general presence or location of nucleic acids may be detected in a static liquid solution, in a flowing stream such as a flow cytometer, in a centrifugation gradient, or in a separation medium, such as a gel or electrophoretic fluid, when leaving the separation medium, or affixed to a solid or semisolid support. Alternatively, the dye may be selective for a particular type of nucleic acid, and the presence, amount or location of particular nucleic acids are selectively detected. Attachment of covalent labels to the polymers used to form the dye-nucleic acid complex does not necessarily prevent subsequent formation of the fluorescent complex.

Nucleic acids may be detected with high sensitivity in a wide variety of solutions and separation media, including electrophoretic gels such as acrylamide and agarose gels, both denaturing and non-denaturing, and in other electrophoretic fluids, such as in capillary electrophoresis. The dyes may or may not give a strong fluorescent signal with small nucleic acids (as few as 8 bases or base pairs with some embodiments) even with very small amounts of nucleic acids. Using a fluorescence microscope, a single nucleic acid molecule may be detectable. Nucleic acid content from as few as 5 mammalian cells may be detected in cell extracts. As little as a few picograms of double-stranded DNA/mL of solution can be detected in a fluorometer. In conjunction with an ultraviolet transilluminator, it is possible to detect as little as 10 picograms of double stranded DNA per band in an electrophoretic gel. Some dyes may give such a bright signal even with illumination by ordinary fluorescent room lights that as little as 1 ng DNA per band is detected. When used for pre- or post-staining of electrophoresis gels, the high sensitivity of the dyes of the present invention may allow for the detection of previously unmeasurable amounts of nucleic acids using inexpensive instrumentation (e.g., UV trans- and epi-illuminators) without requiring destaining.

The presence or location of nucleic acids, stained as described above, may in turn be used to indicate the presence or location of organisms, cells, or organelles containing the nucleic acids, where the presence or location of the fluorescent signal corresponds to the presence or location of the biological structure (e.g., stained cells or organelles). Infective agents such as bacteria, mycoplasma, mycobacteria, viruses and parasitic microorganisms, as well as other cells, may be stained and detected inside eukaryotic cells even though the fluorescent signal generated by an individual virus particle is below the resolution level of standard detection instrumentation. In a further embodiment of the invention, the fluorescent signal resulting from formation of the dye-nucleic acid complex may be used as a basis for sorting cells, for example, sorting stained cells from unstained cells or sorting cells with one set of spectral properties from cells with another set of spectral properties.

In addition to detection of the presence or location of nucleic acids as well as their enclosing structures, the staining profile that results from the formation of the dye-nucleic acid complex is indicative of one or more characteristics of the sample. The staining profile refers to the shape, location, distribution, spectral properties of the profile of fluorescent signals resulting from excitation of the fluorescent dye-nucleic acid complexes. The sample can be characterized simply by staining the sample and detecting the staining profile that is indicative of a characteristic of the sample. More effective characterization is achieved by utilizing a dye that is selective for a certain characteristic of the sample being evaluated or by utilizing an additional reagent (such as is described below), where the additional reagent is selective for the same characteristic to a greater or lesser extent or where the additional reagent is selective for a different characteristic of the same sample. The dyes may exhibit varying degrees of selectivity with regard to nucleic acid structure, location, and cell type and with regard to cell permeability. Some dyes may selectively stain the nucleus while others selectively stain the mitochondria or mitochondrial nucleoids in certain cell types. Others may stain only dead cells (i.e., with compromised cell membranes) while some dyes may selectively give a better signal on RNA than DNA or vice versa. Some may give a greater signal on AT or GC rich polymers while some dyes may be relatively non-selective in staining all nucleic acids, all intracellular nucleic acids, or all cell types.

In one embodiment of the invention, where the dye is selected to be membrane permeable or relatively impermeant to cell membranes, the staining profile that results from the formation of the dye-nucleic acid complex may be indicative of the integrity of the cell membrane, which in turn is indicative of cell viability. The cells may be stained as above for a time period and in a dye concentration sufficient to give a detectable fluorescent signal in cells with compromised membranes. The required time period is dependent on temperature and concentration and can be optimized by standard procedures within the general parameters as previously described. Relatively impermeant dyes of the invention are used to indicate cells where the cell membranes are disrupted. When the dye is selected to be impermeant to cells with intact membranes, formation of the fluorescent dye-nucleic acid complex inside the cell is indicative that the integrity of the cell membrane is disrupted, and the lack of fluorescent dye-nucleic acid complexes inside the cell is indicative that the cell is intact or viable. The impermeant dye is optionally used in conjunction with a counterstain that gives a detectably different signal and is indicative of metabolically active cells or, in combination with the impermeant dye, is indicative of cells with intact membranes. Alternatively, the more permeant dyes of the invention are used to stain both cells with intact membranes and cells with disrupted membranes which, when used in conjunction with a counterstain, gives a detectably different signal in cells with disrupted membranes and allows the differentiation of viable cells from dead cells. The counterstain that gives a detectably different signal in cells with disrupted membranes is optionally an impermeant dye of the invention or another reagent that indicates loss of integrity of the cell membrane or lack of metabolic activity of the dead cells. For example, when the cells are stained with a concentration of dye that is known to stain live bacteria, the relative reduction of a fluorescence intensity can be used to distinguish quiescent bacteria, which are not actively expressing proteins, from metabolically active bacteria.

In a further embodiment of the invention, the shape and distribution of the staining profile of dye-nucleic acid complexes may be indicative of the type of cell or biological structure that contains the stained nucleic acids. Cells may be discriminated by eye based on the visual fluorescent signal or be discriminated by instrumentation as described above based on the spectral properties of the fluorescent signal. For example, dyes that are non-selective for staining nucleic acids in intracellular organelles may be used to identify cells that have an abundance or lack of such organelles, or the presence of micronuclei and other abnormal subparticles containing nucleic acids and characteristic of abnormal or diseased cells. A sample may be characterized as containing blebbing cells or nuclei based on the visible staining profile. Dyes that are selective for the nucleic acids in a particular organelle (e.g., in the nucleus or in mitochondria), even in the presence of limited staining of nucleic acids in the cytoplasm or other organelles, may be used to characterize cells as containing or lacking such organelles based on the intensity as well as the location of the signal, allowing the use of instrumentation to characterize the sample. Typically the staining profile used to characterize the sample is indicative of the presence, shape, or location of organelles or of cells, where the cells are located in a biological fluid, in a tissue, or in other cells.

Furthermore, the differential permeability of bacterial and higher eukaryotic cells to some dyes may allow for selective staining of live mammalian cells with little or no staining of live bacteria. A dye selected to be permeant to bacteria may be used in combination with a dye that is only permeant to eukaryotes to differentiate bacteria in the presence of eukaryotes. Dead bacteria with compromised membranes, such as those in the phagovacuoles of active macrophages or neutrophils, may be rendered permeable to the dyes that are otherwise only permeant to eukaryotes, as a result of toxic agents produced by the phagocytic cells.

In another embodiment of the invention, the staining profile results from the formation of the dye-nucleic acid complex in an electrophoretic gel, or sedimentation or centrifugation gradient. In addition to indicating the presence of nucleic acids in the gel, the staining profile is indicative of one or more characteristics of the nucleic acid solution applied to the gel. The number of bands and/or the intensity of the signal per band of the staining profile, for example, may be indicative of the purity or homogeneity of the nucleic acid solution. Band tightness and degree of smearing may be indicative of the integrity of the nucleic acids in the solution. The size, conformation, and composition of the nucleic acids may be indicated by the relative mobility of the nucleic acid through the gel, which may be used to detect changes caused by interaction of analytes with the nucleic acid such as protein binding or enzymatic activity. In one embodiment, the dyes have low intrinsic fluorescence so there may be no need to destain gels to remove free dye. Furthermore, the fluorescence of the dye-nucleic acid complex may not be quenched by denaturants such as urea and formaldehyde, eliminating the need for their removal from the gels prior to staining In yet another embodiment of the invention, the staining profile may be indicative of the presence or predominance of a type of nucleic acid that is used to characterize the sample. In one embodiment of the invention, the dye is chosen to be more selective for AT or GC rich nucleic acids, such that staining profile may be indicative of the relative proportion of these bases. In another embodiment of the invention, the spectral properties of the nucleic acid-dye complexes may vary depending on the secondary structure of the nucleic acid present in the complex. The spectral properties may vary in fluorescence enhancement, fluorescence polarization, fluorescence lifetime, excitation wavelength or emission wavelength. A comparison of the fluorescence response of a sample of unknown nucleic acids with that of a stained nucleic acid of known secondary structure may allow the secondary structure of the unknown nucleic acids to be determined, and the amount of nucleic acids in the sample to be quantified. In this manner, RNA and single stranded DNA may be differentiated from double stranded DNA. When nuclease is added to the nucleic acids in solution or in fixed cells to digest the RNA or DNA prior to combining with the dye, the fluorescent signal from the dye-nucleic acid complexes can be used to discriminate the nucleic acid that was not digested in the presence of the nuclease from undigested nucleic acids.

This same property of sensitivity to secondary structure by monomethine dyes may be used to quantitate double stranded nucleic acids in the presence of single stranded nucleic acids. Samples containing both double stranded and single stranded DNA or RNA may yield emission maxima in both the green and longer wavelength regions at high dye:base ratios. Meaningful information about the amounts of single stranded and double stranded nucleic acids in solution may be gathered by a direct comparison of the spectra of the low dye ratio sample and high dye ratio sample. For example, where a nucleic acid solution such as purified oligonucleotides, DNA amplification reactions, a cDNA synthesis, plasmid preparation, or cell extraction is stained with a high dye concentration (i.e., greater than or equal to the concentration of nucleic acid bases), the fluorescent signal that results from complexes formed by single stranded nucleic acids is red-shifted from the fluorescent signal formed by double stranded nucleic acids. When the dye is selected to give a high quantum yield with double stranded nucleic acids and the quantum yield of the red-shifted fluorescent signal is minimal, the quantum yield of the stronger signal may be used to quantitate the amount of double stranded nucleic acid in the sample, even in the presence of single stranded nucleic acids.

The nucleic acids for this and other applications may be quantitated by comparison of the detectable fluorescent signal from the dye-nucleic acid complexes with a fluorescent standard characteristic of a given amount of nucleic acid. When one type of nucleic acid in a sample may be selectively digested to completion, the fluorescent signal can be used to quantitate the nucleic acid remaining after digestion. Alternatively, prior to being stained, a solution of nucleic acids may be separated into discrete fractions using standard separation techniques and the amount of nucleic acid present in each fraction may be quantitated using the intensity of the fluorescent signal that corresponds to that portion. The solution may contain purified synthetic or natural nucleic acids or crude mixtures of cell extracts or tissue homogenates. When aliquots from a single sample are taken over time, and the nucleic acid content of each aliquot is quantitated, the rate of cell or nucleic acid proliferation may be readily determined from the change in the corresponding fluorescence over time.

In another aspect of the invention, the dye-nucleic acid complexes are used as a fluorescent tracer or as probe for the presence of an analyte. In one aspect of the invention, dye-nucleic acid complexes are used as a size or mobility standard, such as in electrophoresis or flow cytometry. Alternatively, the fluorescent signal that results from the interaction of the dye with nucleic acids may be used to detect or quantitate the activity or presence of other molecules that interact with nucleic acids. The nucleic acids used to form the dye-nucleic acid complex are optionally attached to a solid or semi-solid support, such as described above, or is free in solution, or is enclosed in a biological structure. Such molecules include but are not limited to drugs, other dyes, proteins such as histones or double stranded or single stranded DNA or RNA binding proteins, or enzymes such as endonucleases or topoisomerases. In one aspect of the invention, a dye having a binding affinity for nucleic acid greater than that of the analyte being assayed displaces the analyte or prevents the interaction of the analyte with the nucleic acid. For example, DNA templates that are heavily bound with a high affinity dye (i.e., at ratios of greater than 3 bp:dye molecule in the staining solution) may be protected from DNase I activity.

For instance, the dyes having a binding affinity greater than $10^{-6}$ M, e.g., greater than $10^{-8}$ M, may be effective to displace analytes that interact with nucleic acids. Dye affinity may be determined by measuring the fluorescence of the dye-nucleic acid complexes, fitting the resulting data to an equilibrium equation and solving for the association constant. In another aspect of the invention, dyes having a binding affinity that may be less than that of the analyte being assayed may be displaced from the dye-nucleic acid complex by the presence of the analyte, with a resultant loss of fluorescence. For example, lower affinity dye molecules prebound to double-stranded DNA may be displaced by histones.

In one embodiment, complexes are used as an indicator of enzymatic activity, that is, as a substrate for nucleases, topoisomerases, gyrases, and other enzymes that interact with nucleic acids. Alternatively, the complex may be used to quantitate the abundance of proteins (such as histones) that bind nucleic acids, or of DNA binding drugs (such as distamycin, spermine, actinomycin, mithramycin, chromomycin). The fluorescent complex may be combined with the sample thought to contain the analyte and the resultant increase or decrease in fluorescent signal qualitatively or quantitatively may indicate the presence of the analyte.

Additional Reagents

The dyes can be used in conjunction with one or more additional reagents that are separately detectable. The additional reagents may be separately detectable if they are used separately, e.g., used to stain different aliquots of the same sample or if they stain different parts or components of a sample, regardless of whether the signal of the additional reagents is detectably different from the fluorescent signal of the dye-nucleic acid complex. Alternatively, the dye of the invention may be selected to give a detectable response that is different from that of other reagents desired to be used in combination with the subject dyes. For example, the additional reagent or reagents may be fluorescent and have different spectral properties from those of the dye-nucleic acid complexes. For example, dyes that form complexes that permit excitation beyond 600 nm may be used in combination with commonly used fluorescent antibodies such as those labeled with fluorescein isothiocyanate or phycoerythrin.

Any fluorescence detection system (including visual inspection) may be used to detect differences in spectral properties between dyes with differing levels of sensitivity. Such differences include, but are not limited to, a difference in excitation maxima, a difference in emission maxima, a difference in fluorescence lifetimes, a difference in fluorescence emission intensity at the same excitation wavelength or at a different wavelength, a difference in absorptivity, a difference in fluorescence polarization, a difference in fluorescence enhancement in combination with target materials, or combinations thereof. The detectably different dye may be one of the dyes of the invention having different spectral properties and/or different selectivity. In one aspect of the invention, the dye-nucleic acid complexes and the additional detection reagents may have the same or overlapping excitation spectra, but possess visibly different emission spectra, generally having emission maxima separated by >10 nm, e.g., >20 nm or >50 nm. Simultaneous excitation of all fluorescent reagents may require excitation of the sample at a wavelength that is suboptimal for each reagent individually, but optimal for the combination of reagents. Alternatively, the additional reagent(s) may be simultaneously or sequentially excited at a wavelength that is different from that used to excite the subject dye-nucleic acid complex. In yet another alternative, one or more additional reagents may be used to quench or partially quench the fluorescence of the dye-nucleic acid complexes, such as by adding a second reagent to improve the selectivity for a particular nucleic acid or the AT/GC selectivity.

The additional dyes may optionally be used to differentiate cells or cell-free samples containing nucleic acids according to size, shape, metabolic state, physiological condition, genotype, or other biological parameters, or combinations thereof. The additional reagent is optionally selective for a particular characteristic of the sample for use in conjunction with a non-selective reagent for the same characteristic, or may be selective for one characteristic of the sample for use in conjunction with a reagent that is selective for another characteristic of the sample. In one aspect of the invention, the additional dye or dyes may be metabolized intracellularly to give a fluorescent product inside certain cells but not inside other cells, so that the fluorescence response of the dye of the invention predominates only where such metabolic process is not taking place. Alternatively, the additional dye or dyes may be specific for some external component of the cell such as cell surface proteins or receptors, e.g., fluorescent lectins or antibodies. In yet another aspect of the invention, the additional dye or dyes may actively or passively cross the cell membrane and may be used to indicate the integrity or functioning of the cell membrane (e.g., calcein AM or BCECF AM). In another aspect, the additional reagents bind selectively to AT-rich nucleic acids and may be used to indicate chromosome banding. In another aspect of the invention, the additional reagent is an organelle stain, i.e., a stain that is selective for a particular organelle, for example, the additional reagent(s) may be selected for potential sensitive uptake into the mitochondria (e.g., rhodamine 123 or tetramethyl rodamine) or for uptake due to pH gradient in an organelle of a live cell.

The additional dyes are added to the sample being analyzed to be present in an effective amount, with the optimal concentration of dye determined by standard procedures generally known in the art. Each dye may be prepared in a separate solution or combined in one solution, depending on the intended use. After illumination of the dyed cells at a suitable wavelength, as above, the cells may be analyzed according to their fluorescence response to the illumination. In addition, the differential fluorescence response may be used as a basis for sorting the cells or nucleic acids for further analysis or experimentation. For example, all cells that "survive" a certain procedure may be sorted, or all cells of a certain type in a sample may be sorted. The cells may be sorted manually or using an automated technique such as flow cytometry, according to the procedures known in the art, such as in U.S. Pat. No. 4,665,024).

The examples below are given so as to illustrate the practice of this invention. They are not intended to limit or define the entire scope of this invention.

Example 1

Examples of compounds of the invention can be prepared as follows.

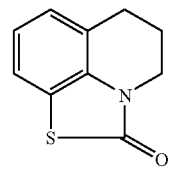 [SMILES: O=c1sc2cccc3c2n1CCC3]

5,6-Dihydrothiazolo[5,4,3-ij]quinolin-2(4H)-one

To 1,2,3,4-tetrahydroquinoline (2 ml, 15.9 mmol) in 10 ml o-dichlorobenzene was added slowly chlorocarbonylsulfenyl chloride (1.3 ml, 15.9 mol) by syringe. The exothermic reaction was allowed to continue to heat from 70° C. to 80° C. for 4 hours by means of an oil bath. At this point the mixture was cooled to room temperature and the solvent removed under reduced pressure. The crude product was then purified by silica gel column chromatography eluting with 30% ethyl acetate in heptane. 2.48 g (81.5% yield) of a white solid was isolated: $^1$H NMR (d$_6$-DMSO) δ 7.43 (d, 1H, Ar), 7.09 (dd, H, Ar), 7.08 (d, H, Ar), 3.83 (m, 2H, CH$_2$—N), 2.81 (t, 2H, CH$_2$—Ar), 1.98 (m, 2H, —CH$_2$—). Mass spectrum, m/e Calcd for C$_{10}$H$_{10}$NOS$^+$: 192.1. Found: 192.1.

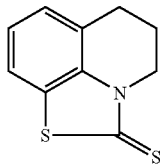

5,6-Dihydrothiazolo[5,4,3-ij]quinoline-2(4H)-thione

The above compound (2 g, 10.4 mmol) and phosphorous pentasulfide (1.16 g, 2.6 mmol) were refluxed in 20 ml xylenes for 2 hours. After the xylenes were removed from the reaction mixture, the product was extracted into dichloromethane containing 5% methanol, washed with saturated sodium bicarbonate, followed by a water wash. The organic fraction was then dried with sodium sulfate, filtered and subjected to rotary evaporation. A quantitative yield of the white product was isolated: Mass spectrum, m/e Calcd for C$_{10}$H$_{10}$NS$_2^+$: 208. Found: 208.

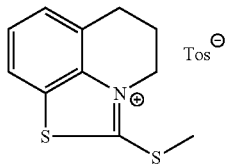

1-(Methylthio)-7,8-dihydro-6H-thiazolo[5,4,3-ij] quinolin-9-ium p-toluenesulfonate The above thione (2.16 g, 10.4 mmol) and methyl p-toluenesulfonate (3 ml, 19.8 mmol) were refluxed in 20 ml xylenes for 2 hours. After the xylenes were evaporated from the reaction mixture, the product was triturated three times with ether. A quantitative yield of the orange product was isolated after extensive drying in vacuo: $^1$H NMR (d$_6$-DMSO) δ 8.15 (d, 2H, Tos), 7.73 (d, 2H, Tos), 7.56 (dd, 1H, Ar), 7.45 (d, H, Ar), 7.08 (d, H, Ar), 4.32 (m, 2H, CH$_2$—N), 3.09 (s, 3H, CH$_3$-Tos), 3.01 (t, 2H, CH$_2$—Ar), 2.26 (s, 3H, CH$_3$—S), 2.22 (m, 2H, —CH$_2$—). Mass spectrum, m/e Calcd for C$_{11}$H$_{12}$NS$_2^+$: 222.0. Found: 222.1.

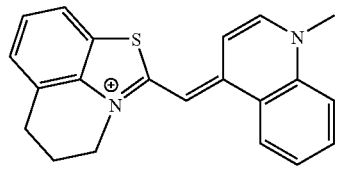 [SMILES: CN1C=C/C(=C\c2sc3cccc4c3[n+]2CCC4)c2ccccc21]

1-((1-Methylquinolin-4(1H)-ylidene)methyl)-7,8-dihydro-6H-thiazolo[5,4,3-ij]quinolin-9-ium (Compound 3632)

1,4-Dimethylquinolinium iodide (403 mg, 1.4 mmol) and 1-(Methylthio)-7,8-dihydro-6H-thiazolo[5,4,3-ij]quinolin-9-ium p-toluenesulfonate (555 mg, 1.4 mmol) were dissolved in 10 ml anhydrous dichloromethane under nitrogen. To this stirred mixture was added triethylamine (590 µL, 4.2 mmol) via syringe. The color of the reaction turned from orange to deep red upon addition of the base. After stirring at room temperature for 4 hours, the mixture was subjected to a silica gel chromatography eluting with 5% methanol and 5% acetic acid in dichloromethane. 470 mg (~73%) of a red solid was isolated: $^1$H NMR (d$_6$-DMSO) δ 8.76 (d, 1H, Ar), 8.54 (d, 1H, Ar), 7.99 (m, 2H, Ar), 7.84 (d, 1H, Ar), 7.73 (t, 1H, Ar), 7.30 (m, 3H, Ar), 6.88 (s, 1H, CH=), 4.48 (t, 2H, CH$_2$—N), 4.12 (s, 3H, CH$_3$—), 2.97 (t, 2H, CH$_2$—Ar), 2.22 (m, 2H, —CH$_2$—). Mass spectrum, m/e Calcd for C$_{21}$H$_{19}$N$_2$S$^+$: 331.1. Found: 331.2. Ex λ=504 nm; Em λ (ds DNA)=529 nm.

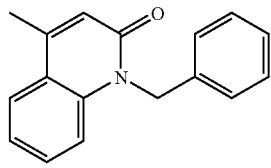 [SMILES: Cc1cc(=O)n(Cc2ccccc2)c2ccccc12]

1-benzyl-4-methylquinolin-2(1H)-one

2-Hydroxy-4-methyl-quinoline (4.32 g, 27.1 mmol), potassium carbonate (5.63 g, 40.7 mmol), and DMF (50 mL) were stirred in a 250 mL flask under nitrogen atmosphere at RT. Benzyl bromide (6.96 g, 40.7 mmol) was added via syringe and the reaction was heated to 110° C. for 3 h. The reaction was diluted with EtOAc, washed with water, dried over Na$_2$SO$_4$, filtered and evaporated to give a yellow solid. The crude product is purified by column chromatography (SiO$_2$, 1:1 EtOAc:Heptane) to give 2.95 g (62%) of a white solid: $^1$H-NMR (CD$_2$Cl$_2$) δ 2.55 (s, 3H), 5.55 (s, 2H), 6.63 (s, 1H), 7.23 (m, 7H), 7.42 (t, 1H, J=6 Hz), 7.78 (d, 1H, J=9 Hz); Anal. Calcd for C$_{17}$H$_{16}$NO (M+H): 250.12. Found 250.1 (M+H, ESI+).

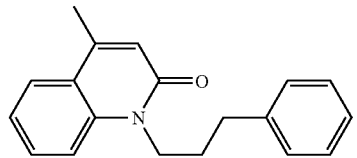 [SMILES: Cc1cc(=O)n(CCCc2ccccc2)c2ccccc12]

4-Methyl-1-(3-phenylpropyl)quinolin-2(1H)-one

To a mixture of 2-Hydroxy-4-methylquinoline (1.0 g, 6.28 mmol) and K$_2$CO$_3$ (1.302 g, 9.42 mmol) in 10 mL dry DMF was added 1-Bromo-3-phenylpropane (1.43 mL, 9.42 mmol) and the mixture was heated to 60° C. overnight. Volatiles were removed under reduced pressure giving a yellow solid that was suspended in EtOAc and filtered. The filtrate was concentrated and purified on silica gel to give the product as a white solid. $^1$NMR (300 MHz, CDCl$_3$): δ 7.71 (d, 1H), 7.49 (t, 1H), 7.24 (m, 7H), 6.65 (s, 1H), 4.32 (t, 2H), 2.28 (t, 2H), 2.46 (s, 3H), 2.06 (m, 2H) ppm; Mass spectrum, m/e Calcd for C$_{19}$H$_{19}$NO: 278.15. Found: 278.2.

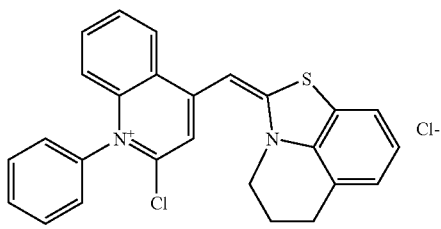 [SMILES: Clc1cc(/C=C2/Sc3cccc4c3N2CCC4)c2ccccc2[n+]1-c1ccccc1 ; [Cl-]]

2-Chloro-4-((5,6-dihydrothiazolo[5,4,3-ij]quinolin-2 (4H)-ylidene)methyl)-1-phenylquinolinium chloride The title compound (0.27 g) was synthesized from 1-phenyl-4-methyl-2-quinolone (0.4 g) and 1-(methylthio)-7,8-dihydro-6H-thiazolo[5,4,3-ij]quinolin-9-ium tosylate (0.54 g) according to the procedure in U.S. Pat. No. 5,658,751. Mass spectrum, m/e Calcd for C$_{26}$H$_{20}$ClN$_2$S$^+$: 427. Found: 427.

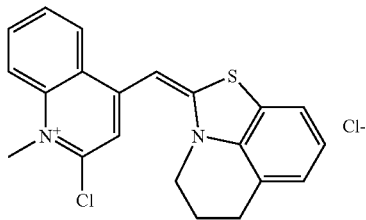 [SMILES: C[n+]1c(Cl)cc(/C=C2/Sc3cccc4c3N2CCC4)c2ccccc21 ; [Cl-]]

2-chloro-4-((5,6-dihydrothiazolo[5,4,3-ij]quinolin-2 (4H)-ylidene)methyl)-1-methylquinolinium chloride The title compound (53 mg) was synthesized from 1,4-dimethyl-2-quinolone (0.20 g) and 1-(methylthio)-7,8-dihydro-6H-thiazolo[5,4,3-ij]quinolin-9-ium tosylate (0.36 g) according to the procedure in U.S. Pat. No. 5,658,751. Mass spectrum, m/e Calcd for C$_{21}$H$_{18}$ClN$_2$S$^+$: 365. Found: 365.

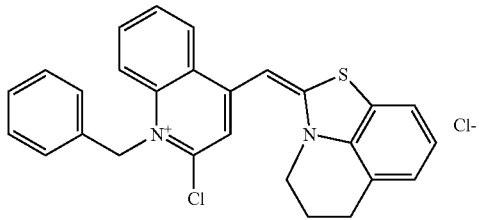 [SMILES: Clc1cc(/C=C2/Sc3cccc4c3N2CCC4)c2ccccc2[n+]1Cc1ccccc1 ; [Cl-]]

2-chloro-4-((5,6-dihydrothiazolo[5,4,3-ij]quinolin-2 (4H)-ylidene)methyl)-1-benzylquinolinium chloride The title compound (0.13 g) was synthesized from 1-benzyl-4-methyl-2-quinolone (0.25 g) and 1-(methylthio)-7,8-dihydro-6H-thiazolo[5,4,3-ij]quinolin-9-ium tosylate (0.32 g) according to the procedure in U.S. Pat. No. 5,658,751. Mass spectrum, m/e Calcd for C$_{27}$H$_{22}$ClN$_2$S$^+$: 441. Found: 441.

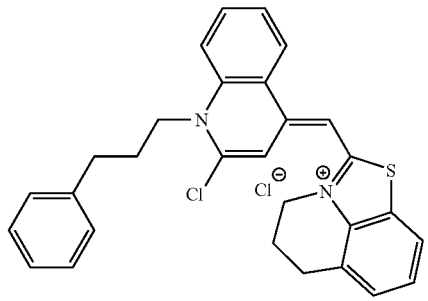 [SMILES: ClC1=C/C(=C\c2sc3cccc4c3[n+]2CCC4)c2ccccc2N1CCCc1ccccc1 ; [Cl-]]

1-((2-Chloro-1-(3-phenylpropyl)quinolin-4(1H)-ylidene)methyl)-7,8-dihydro-6H-thiazolo[5,4,3-ij]quinolin-9-ium chloride The title compound (79 mg) was synthesized from 4-methyl-1-(3-phenylpropyl)quinolin-2(1H)-one (0.37 g) and 1-(methylthio)-7,8-dihydro-6H-thiazolo[5,4,3-ij]quinolin-9-ium tosylate (0.49 g) according to the procedure in U.S. Pat. No. 5,658,751. Mass spectrum, m/e Calcd for C$_{29}$H$_{26}$ClN$_2$S: 469.15. Found: 469.3.

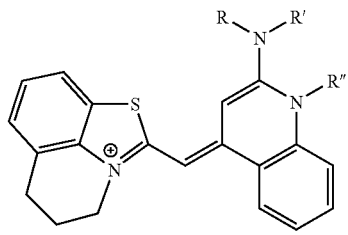

General Method for the Preparation of Amino Quinolinium Dihydrothiozolo-Quinolinium Cyanines The appropriate 1-((2-chloro-1-(R″)quinolin-4(1H)-ylidene)methyl)-7,8-dihydro-6H-thiazolo[5,4,3-ij]quinolin-9-ium was dissolved in dichloromethane. An excess of amine was added to the stirring solution. After 2 to 18 hours the solvent was removed and the crude product purified by preparative HPLC using 0.1% aqueous TFA and acetonitrile as eluting solvents.

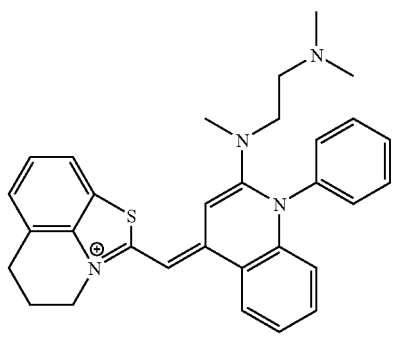 [SMILES: CN(C)CCN(C)C1=C/C(=C\c2sc3cccc4c3[n+]2CCC4)c2ccccc2N1c1ccccc1]

1-((2-((2-(Dimethylamino)ethyl)(methyl)amino)-1-phenylquinolin-4(1H)-ylidene)methyl)-7,8-dihydro-6H-thiazolo[5,4,3-ij]quinolin-9-ium (Compound 3568)

Starting with 1-((2-chloro-1-phenylquinolin-4(1H)-ylidene)methyl)-7,8-dihydro-6H-thiazolo[5,4,3-ij]quinolin-9-ium (21 mg) and an excess of N,N,N-trimethylethane-1,2-diamine a total of 8.1 mg (~33% yield) of the title compound was obtained: Mass spectrum, m/e Calcd for $C_{31}H_{33}N_4S^+$: 493.2. Found: 493.3. Ex λ=466 nm; Em λ (ds DNA)=529 nm.

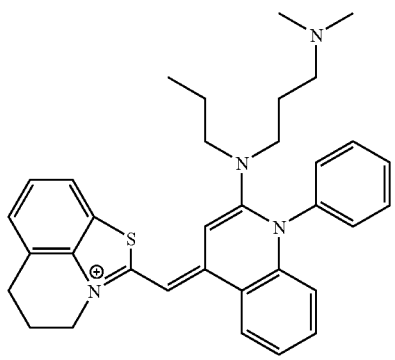 [SMILES: CCCN(CCCN(C)C)C1=C/C(=C\c2sc3cccc4c3[n+]2CCC4)c2ccccc2N1c1ccccc1]

1-((2-((3-(Dimethylamino)propyl)(propyl)amino)-1-phenylquinolin-4(1H)-ylidene)methyl)-7,8-dihydro-6H-thiazolo[5,4,3-ij]quinolin-9-ium (Compound 3654)

Starting with 1-((2-chloro-1-phenylquinolin-4(1H)-ylidene)methyl)-7,8-dihydro-6H-thiazolo[5,4,3-ij]quinolin-9-ium (30 mg) and an excess of N,N-dimethyl-N-propylpropane-1,3-diamine a total of 4 mg (~11% yield) of the title compound was obtained: Mass spectrum, m/e Calcd for $C_{34}H_{39}N_4S^+$: 535.3. Found: 535.3. Ex λ=498 nm; Em λ (ds DNA)=529 nm.

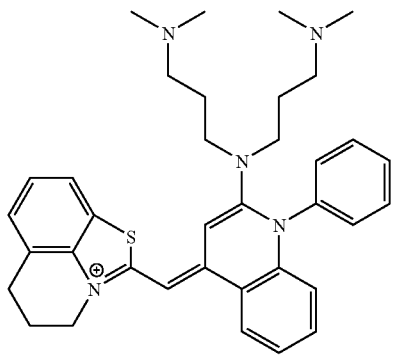 [SMILES: CN(C)CCCN(CCCN(C)C)C1=C/C(=C\c2sc3cccc4c3[n+]2CCC4)c2ccccc2N1c1ccccc1]

1-((2-(Bis(3-(dimethylamino)propyl)amino)-1-phenylquinolin-4(1H)-ylidene)methyl)-7,8-dihydro-6H-thiazolo[5,4,3-ij]quinolin-9-ium (PBI 3646)

Starting with 1-((2-chloro-1-phenylquinolin-4(1H)-ylidene)methyl)-7,8-dihydro-6H-thiazolo[5,4,3-ij]quinolin-9-ium (430 mg) and an excess of N-(3-(dimethylamino)propyl)-N,N-dimethylpropane-1,3-diamine a total of 36.5 mg (~6% yield) of the title compound was obtained: Mass spectrum, m/e Calcd for $C_{36}H_{44}N_5S^+$: 578.3. Found: 578.3. Ex λ=504 nm; Em λ (ds DNA)=531 nm.

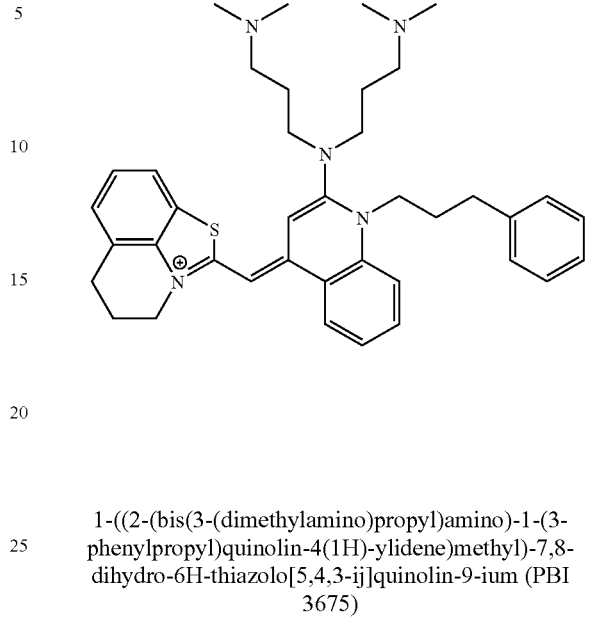

1-((2-(bis(3-(dimethylamino)propyl)amino)-1-(3-phenylpropyl)quinolin-4(1H)-ylidene)methyl)-7,8-dihydro-6H-thiazolo[5,4,3-ij]quinolin-9-ium (PBI 3675)

Starting with 1-((2-chloro-1-(3-phenylpropyl)quinolin-4(1H)-ylidene)methyl)-7,8-dihydro-6H-thiazolo[5,4,3-ij]quinolin-9-ium (70 mg) and an excess of N-(3-(dimethylamino)propyl)-N,N-dimethylpropane-1,3-diamine a total of 67 mg (~66% yield) of the title compound was obtained: Mass spectrum, m/e Calcd for $C_{39}H_{50}N_5S^+$: 620.4. Found: 620.5. Ex λ=503 nm; Em λ (ds DNA)=535 nm.

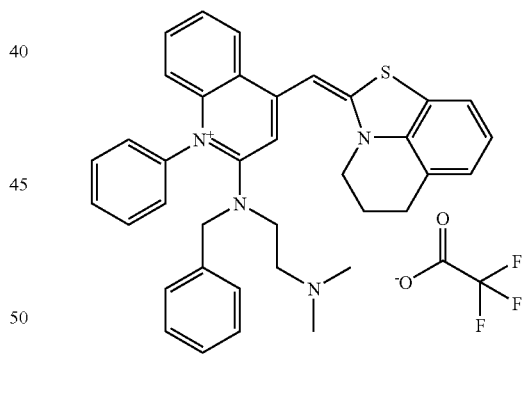

2-(benzyl(2-(dimethylamino)ethyl)amino)-4-((5,6-dihydrothiazolo[5,4,3-ij]quinolin-2(4H)-ylidene)methyl)-1-phenylquinolinium trifluoroacetate (PBI 3666)

The title compound (1.5 mg) was synthesized from 2-chloro-4-((5,6-dihydrothiazolo[5,4,3-ij]quinolin-2(4H)-ylidene)methyl)-1-phenylquinolinium chloride (64 mg). Mass spectrum, m/e Calcd for $C_{37}H_{37}N_4S^+$: 569. Found: 569.

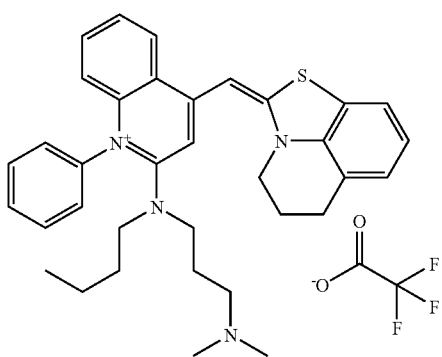

2-(butyl(3-(dimethylamino)propyl)amino)-4-((5,6-dihydrothiazolo[5,4,3-ij]quinolin-2(4H)-ylidene)methyl)-1-phenylquinolinium trifluoroacetate (PBI 3667)

The title compound (3 mg) was synthesized from 2-chloro-4-((5,6-dihydrothiazolo[5,4,3-ij]quinolin-2(4H)-ylidene)methyl)-1-phenylquinolinium chloride (58 mg). Mass spectrum, m/e Calcd for $C_{35}H_{41}N_4S^+$: 549. Found: 549.

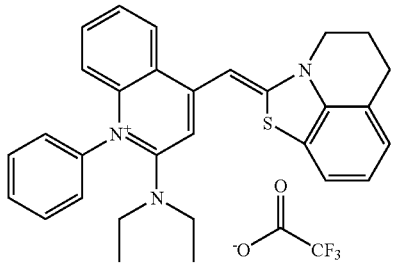

2-(diethylamino)-4-((5,6-dihydrothiazolo[5,4,3-ij]quinolin-2(4H)-ylidene)methyl)-1-phenylquinolinium trifluoroacetate (PBI 3676)

The title compound (8 mg) was synthesized from 2-chloro-4-((5,6-dihydrothiazolo[5,4,3-ij]quinolin-2(4H)-ylidene)methyl)-1 phenylquinolinium chloride (22 mg). Mass spectrum, m/e Calcd for $C_{30}H_{30}N_3S^+$: 464. Found: 464.

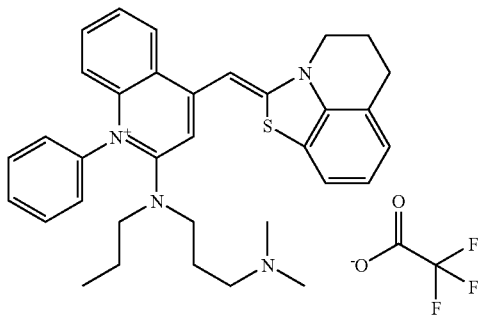

1-benzyl-4-((5,6-dihydrothiazolo[5,4,3-ij]quinolin-2(4H)-ylidene)methyl)-2-((3-(dimethylamino)propyl)(propyl)amino)quinolinium trifluoroacetate (PBI 3677)

The title compound (8 mg) was synthesized from 2 chloro-4-((5,6-dihydrothiazolo[5,4,3-ij]quinolin-2(4H)-ylidene)methyl)-1-benzylquinolinium chloride (130 mg). Mass spectrum, m/e Calcd for $C_{35}H_{41}N_4S^+$: 549. Found: 549.

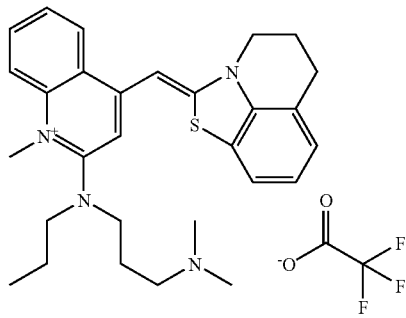

1-methyl-4-((5,6-dihydrothiazolo[5,4,3-ij]quinolin-2(4H)-ylidene)methyl)-2-((3-(dimethylamino)propyl)(propyl)amino)quinolinium trifluoroacetate (PBI 3678)

The title compound (7 mg) was synthesized from 2-chloro-4-((5,6-dihydrothiazolo[5,4,3-ij]quinolin-2(4H)-ylidene)methyl)-1-methylquinolinium chloride (53 mg). Mass spectrum, m/e Calcd for $C_{29}H_{37}N_4S^+$: 473. Found: 473.

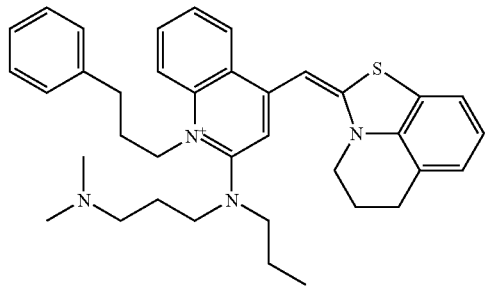 [SMILES: CCCN(CCCN(C)C)c1cc(/C=C2/Sc3cccc4c3N2CCC4)c2ccccc2[n+]1CCCc1ccccc1]

4-((5,6-Dihydrothiazolo[5,4,3-ij]quinolin-2(4H)-ylidene)methyl)-2-((3-(dimethylamino)propyl)(propyl)amino)-1-(3-phenylpropyl)quinolinium (PBI 3679)

Starting with 1-((2-chloro-1-(3-phenylpropyl)quinolin-4(1H)-ylidene)methyl)-7,8-dihydro-6H-thiazolo[5,4,3-ij]quinolin-9-ium (40 mg) and an excess of N,N-dimethyl-N-propylpropane-1,3-diamine a total of 2 mg (~11% yield) of the title compound was obtained: Mass spectrum, m/e Calcd for $C_{37}H_{45}N_4S^+$: 577.84. Found: 577.3. Abs. $\lambda_{max}$=499 nm; Em $\lambda_{max}$=533 nm; $\Phi$=0.34.

TABLE 1

Summary of quantum yield (Φ), absorbance (λ$_{Ex}$),
and emission (λ$_{max}$Em) data for select compounds.

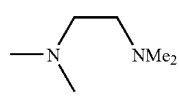

| Cmpd. # | Z | R | Φ dsDNA | λ$_{Ex}$ dsDNA | λ$_{max}$Em dsDNA |
|---|---|---|---|---|---|
| 3632 | H | Me | 0.2 | 504 | 529 |
| 3568 | —N(Me)CH₂CH₂NMe₂ | Ph | 0.39 | 466 | 529 |
| 3646 | —N(CH₂CH₂NMe₂)CH₂CH₂CH₂NMe₂ | Ph | 0.43 | 504 | 531 |
| 3654 | —N(nBu)CH₂CH₂CH₂NMe₂ | Ph | 0.70 | 498 | 529 |
| 3666 | —N(CH₂Ph)CH₂CH₂NMe₂ | Ph | 0.34 | 494 | 535 |
| 3667 | —N(nBu)CH₂CH₂NMe₂ | Ph | 0.68 | 494 | 529 |
| 3675 | —N(CH₂CH₂NMe₂)CH₂CH₂CH₂NMe₂ | (CH₂)₃Ph | 0.31 | 503 | 535 |
| 3676 | —NEt₂ | Ph | 0.48 | 494 | 527 |
| 3677 | —N(nBu)CH₂CH₂NMe₂ | CH₂Ph | 0.72 | 494 | 533 |
| 3678 | —N(nBu)CH₂CH₂NMe₂ | Me | 0.68 | 494 | 529 |
| 3679 | —N(nBu)CH₂CH₂NMe₂ | (CH₂)₃Ph | 0.34 | 499 | 533 |

TABLE 1-continued

Summary of quantum yield (Φ), absorbance (λ$_{Ex}$), and emission (λ$_{max}$Em) data for select compounds.

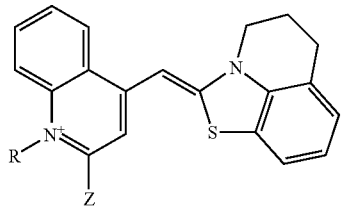

| Cmpd. # | Z | R | Φ dsDNA | λ$_{Ex}$ dsDNA | λ$_{max}$Em dsDNA |
|---|---|---|---|---|---|

Example 2

Examples of compounds of the invention can be prepared as follows

N-(3-methoxyphenyl)-3-oxobutanamide

Ethyl acetoacetate (190 mL, 1.5 moles) was transferred into a 500 mL round-bottom flask with a distillation apparatus. After the temperature was increased to 150-160° C. with oil bath, m-anisidine (33.6 mL, 0.3 moles) was added dropwise into the flask in 20-30 minutes. After the addition, the reaction was kept running until no more ethanol was distilled out. Then, the temperature was decreased to around 90° C. and the excess of ethyl acetoacetate was removed under high vacuum. The residue was recrystallized in iso-propanol and 36 g of white solid was obtained. MS$^+$ 208.1; $^1$HNMR (CD$_2$Cl$_2$) δ ppm 7.28-7.18 (m, 2H), 7.08-7.00 (d, 1H), 6.70-6.62 (d, 1H), 3.80 (s, 3H), 3.58 (s, 2H), 2.30 (s, 3H).

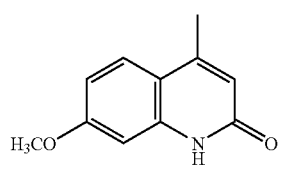

7-methoxy-4-methylquinolin-2(1H)-one

N-(3-methoxyphenyl)-3-oxobutanamide (1 g, 4.8 mmoles) was mixed with polyphosphoric acid (30 g) in a 250 mL flask. The mixture was stirred at 100° C. under nitrogen for 2 hours, poured into 200 mL of water, and potassium carbonate solution was used to adjust pH to 7. The cyclized compound was extracted with ethyl acetate. After purified with column (heptanes/THF), 690 mg of white solid was obtained. MS$^+$ 190.0; $^1$HNMR (CD$_3$OD) δ ppm 7.74-7.64 (d, 1H), 6.95-6.80 (m, 2H), 6.32 (s, 1H), 3.82 (s, 3H), 2.42 (s, 3H).

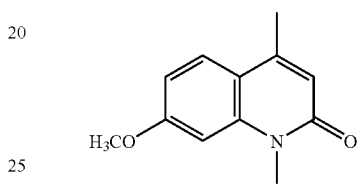

7-Methoxy-1,4-dimethylquinolin-2-one

KOH (670 mg, 12 mmoles) was transferred into 5 mL of DMF, and the suspension was stirred at room temperature for 1 hour. 7-methoxy-4-methylquinolin-2(1H)-one (189 mg, 1 mmole) was transferred into the solution, and the mixture was stirred at 55° C. overnight. When the reaction was over, the solution was poured into 50 mL of water, and the methylated compound was extracted with ethyl acetate 25 mL×3. The combined organic layer was dried with Na$_2$SO$_4$. The desired compound was purified with column (Heptane/THF) and 120 mg of white solid was obtained. MS 204.1; $^1$HNMR (CD$_2$Cl$_2$) δ ppm 7.64-7.60 (d, 1H), 6.86-6.82 (dd, 1H), 6.81 (d, 1H), 6.38 (s, 1H), 3.93 (s, 3H), 3.61 (s, 3H), 2.40 (s, 3H).

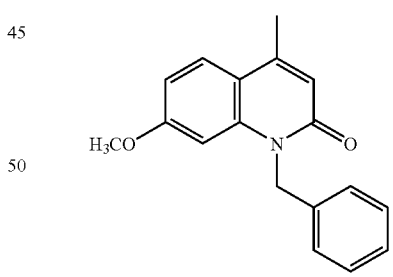

N-Benzyl-7-methoxy-4-methylquinolin-2-one 7-methoxy-4-methylquinolin-2(1H)-one (189 mg, 1 mmole), Benzyl bromide (250 mg, 1.5 mmoles) and Cesium carbonate (500 mg, 1.5 mmoles) were mixed with 5 mL of DMF, and the suspension was stirred at 120° C. under nitrogen for 2.5 hours. When the reaction was over, the solution was poured into 50 mL of water, and the benzylated compound was extracted with ethyl acetate 25 mL×3. The combined organic layer was dried with Na$_2$SO$_4$. The desired compound was purified with column (Heptane/THF) and 125 mg of white solid was obtained. MS+ 280.2; ¹HNMR (CD₂Cl₂) δ ppm 7.65 (d, 1H), 7.36-7.20 (m, 5H), 6.85-6.75 (dd, 1H), 6.70 (d, 1H), 6.49 (s, 1H), 5.49 (s, 2H), 3.75 (s, 3H), 2.47 (s, 3H).

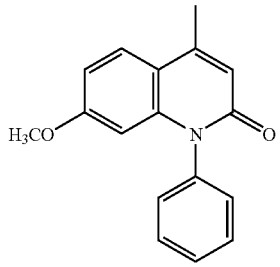 [SMILES: COc1ccc2c(C)cc(=O)n(-c3ccccc3)c2c1]

N-Phenyl-7-methoxy-4-methylquinolin-2-one 7-methoxy-4-methylquinolin-2(1H)-one (189 mg, 1 mmole), Iodobenzene (200 μL, 1.8 mmoles), copper powder (300 mg, 4.7 mmoles) and Potassium carbonate (138 mg, 1 mmole) were mixed with 5 mL of N,N-dimethyl acetamide, and the suspension was stirred at 170° C. under nitrogen overnight. When the reaction was over, the solution was poured into 50 mL of water, and the benzylated compound was extracted with ethyl acetate 25 mL×3. The combined organic layer was dried with Na₂SO₄. The desired compound was purified with column (Heptane/THF) and 120 mg of white solid was obtained. MS+ 266.1; ¹HNMR (CD₂Cl₂) δ ppm 7.70-7.50 (m, 4H), 7.30-7.24 (m, 2H), 6.84-6.78 (dd, 1H), 6.44 (s, 1H), 6.10-6.08 (s, 1H), 3.65 (s, 3H), 2.50 (s, 3H).

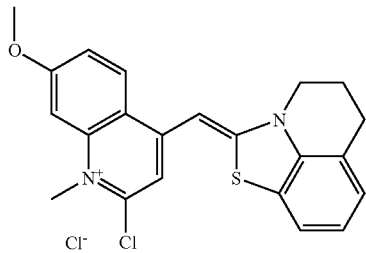 [SMILES: COc1ccc2c(/C=C3\Sc4cccc5c4N3CCC5)cc(Cl)[n+](C)c2c1 ; [Cl-]]

2-chloro-4-((5,6-dihydrothiazolo[5,4,3-ij]quinolin-2 (4H)-ylidene)methyl)-7-methoxy-1-methylquino-linium chloride 7-Methoxy-1,4-dimethylquinolin-2-one (101 mg, 0.5 mmoles) and 5,6-dihydrothiazolo[5,4,3-ij]quinolin-2(4H)-one (480 mg, 2.5 mmoles) were dissolved in 20 mL of acetonitrile in a 100 mL round-bottom flask. Phosphorus oxychloride (415 μL, 4.5 mmoles) was injected into the solution, and the solution was stirred at 80° C. overnight. Then, the temperature was decreased to 0-4° C. with ice/water bath, and a solution a triethylamine (3.9 mL) in acetonitrile (10 mL) was added drop-wise into the reaction flask in 7 minutes. After stirring for another 5 minutes, the reaction was quenched by adding 35 mL of 1N HCl. Most of the acetonitrile was removed under reduced pressure, and the desired compound was extracted by ethyl acetate, purified with column (THF/ DCM/MeOH), and 120 mg of orange color solid was obtained. MS+ 395.2

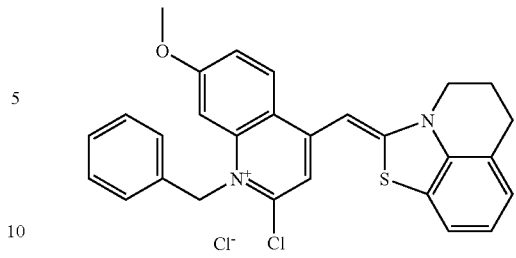

1-Benzyl-2-chloro-4-((5,6-dihydrothiazolo[5,4,3-ij] quinolin-2(4H)-ylidene)methyl)-7-methoxyquino-linium chloride N-Benzyl-7-methoxy-4-methylquinolin-2-one (100 mg, 0.36 mmoles) and 5,6-dihydrothiazolo[5,4,3-ij]quinolin-2 (4H)-one (344 mg, 1.8 mmoles) were dissolved in 20 mL of acetonitrile in a 100 mL round-bottom flask. Phosphorus oxychloride (300 μL, 3.2 mmoles) was injected into the solution, and the solution was stirred at 80° C. overnight. Then, the temperature was decreased to 0-4° C. with ice/water bath, and a solution a triethylamine (2.8 mL) in acetonitrile (10 mL) was added drop-wise into the reaction flask in 7 minutes. After stirring for another 5 minutes, the reaction was quenched by adding 25 mL of 1N HCl. Most of the acetonitrile was removed under reduced pressure, and the desired compound was extracted by ethyl acetate, purified with column (THF/DCM/MeOH), and 44 mg of orange color solid was obtained. MS+ 471.3

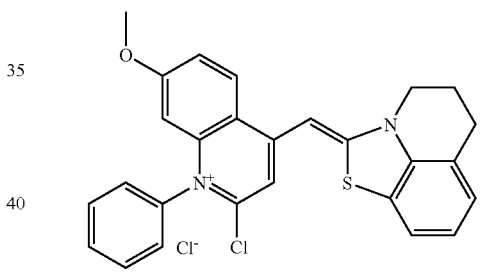

1-Phenyl-2-Chloro-4-((5,6-dihydrothiazolo[5,4,3-ij] quinolin-2(4H)-ylidene)methyl)-7-methoxyquino-linium chloride N-Phenyl-7-methoxy-4-methylquinolin-2-one (110 mg, 0.41 mmoles) and 5,6-dihydrothiazolo[5,4,3-ij]quinolin-2 (4H)-one (400 mg, 2 mmoles) were dissolved in 20 mL of acetonitrile in a 100 mL round-bottom flask. Phosphorus oxychloride (340 μL, 3.7 mmoles) was injected into the solution, and the solution was stirred at 80° C. overnight. Then, the temperature was decreased to 0-4° C. with ice/water bath, and a solution a triethylamine (3.2 mL) in acetonitrile (10 mL) was added drop-wise into the reaction flask in 7 minutes. After stirring for another 5 minutes, the reaction was quenched by adding 28 mL of 1N HCl. Most of the acetonitrile was removed under reduced pressure, and the desired compound was extracted by ethyl acetate, purified with column (THF/DCM/MeOH), and 73 mg of orange color solid was obtained. MS+ 457.3

Boc-3,3'-Iminobis(N,N-dimethylpropylamine)

Di-t-butyl-dicarbonate (2.4 g, 11 mmoles) was dissolved in 35 mL of dichloromethane and the solution was stirred in ice/water bath, followed by adding drop-wise of a solution of 3,3'-Iminobis(N,N-dimethylpropylamine) (2.2 mL, 10 mmoles) and triethylamine (6.3 mL, 50 mmoles) in 20 mL of dichloromethane. After addition, the solution was stirred at room temperature for 3 hours. Then, the solution was washed twice with water, the solvent was removed under reduced pressure, and 1.6 g of colorless oil was obtained. MS$^+$ 288.2; $^1$HNMR (CD$_2$Cl$_2$) δ ppm 3.24-3.14 (t, 4H), 2.24-2.16 (t, 4H), 2.16 (s, 12H), 1.71-1.59 (m, 4H), 1.44 (s, 9H)

Boc-3,3'-Iminobis(N,N,N-trimethyl-1-propylammonium iodide)

Boc-3,3'-Iminobis(N,N-dimethylpropylamine) (1.6 g, 5.6 mmoles) was dissolved in 10 mL of DMF, followed by adding iodomethane (1.7 mL, 28 mmoles). The solution was stirred at room temperature under nitrogen overnight. After transferred into a centrifuge tube, the solution was mixed with ether. After centrifugation, the ether was decanted and the oil at bottom was washed twice with fresh ether, and after all ether was removed, 3.2 g of yellowish solid was obtained. $^1$HNMR (d6-DMSO) δ ppm 3.29-3.15 (m, 8H), 3.12 (s, 18H), 1.95-1.82 (m, 4H), 1.41 (s, 9H)

3,3'-Iminobis(N,N,N-trimethyl-1-propylammonium iodide)

Boc-3,3'-Iminobis(N,N,N-trimethyl-1-propylammonium iodide) (2.7 g) was dissolved in 20 mL of 50% trifloroacetic acid in dichloromethane, followed by adding 500 μL of triisopropylsilane. The solution was stirred at room temperature for 1.5 hours. Then, the solvent was removed by vacuum, and the residue was washed with ether twice, dried, and 3.1 g of yellowish compound was obtained. MS$^{2+}$ 108.6; $^1$HNMR (d6-DMSO) δ ppm 3.45-3.35 (m, 4H), 3.15-2.95 (m, 22H), 2.12-1.99 (m, 4H)

N-Boc-propyl-(3-N',N'-dimethylaminopropyl)amine

Di-t-butyl-dicarbonate (2.4 g, 11 mmoles) was dissolved in 35 mL of dichloromethane and the solution was stirred in ice/water bath, followed by adding drop-wise of a solution of Propyl-(3-N',N'-dimethylaminopropyl)amine (1.44 g, 10 mmoles) and triethylamine (6.3 mL, 50 mmoles) in 15 mL of dichloromethane. After addition, the solution was stirred at room temperature overnight. Then, the solution was washed twice with water, the solvent was removed under reduced pressure, and 1.7 g of colorless oil was obtained. MS$^+$ 245.1; $^1$HNMR (CD$_2$Cl$_2$) δ ppm 3.22-3.08 (m, 4H), 2.25-2.15 (m, 8H), 1.71-1.59 (m, 2H), 1.59-1.45 (m, 2H), 1.44 (s, 9H), 0.90-0.82 (t, 3H).

3-(N-Boc-propylamino)propyl-N',N',N'-trimethylammonium iodide

N-Boc-propyl-(3-N',N'-dimethylaminopropyl)amine (1.7 g, ~7 mmoles) was dissolved in 5 mL of DMF, followed by adding iodomethane (3 mL, 48 mmoles). The solution was stirred at room temperature under nitrogen overnight. After transferred into a centrifuge tube, the solution was mixed with ether. After centrifugation, the ether was decanted and the oil at bottom was washed twice with fresh ether, and after all ether was removed, 2.9 g of oil-like compound was obtained. MS$^+$ 259.2; $^1$HNMR (d6-DMSO) δ ppm 3.28-3.07 (m, 6H), 3.05 (s, 9H), 1.92-1.80 (m, 2H), 1.52-1.40 (m, 2H), 1.39 (s, 9H), 0.84-0.76 (t, 3H).

3-(propylamino)propyl-N',N',N'-trimethylammonium iodide 3-(N-Boc-propylamino)propyl-N',N',N'-trimethylammonium iodide (2.9 g, ~7 mmoles) was dissolved in 20 mL of 50% trifloroacetic acid in dichloromethane, followed by adding 500 μL of triisopropylsilane. The solution was stirred at room temperature for 1 hour. Then, the solvent was removed by vacuum, and the residue was washed with ether twice, dried, and 3.1 g of yellowish compound was obtained. MS$^+$ 159.1; $^1$HNMR (d6-DMSO) δ ppm 3.42-3.34 (m, 2H), 3.06 (s, 9H), 3.00-2.82 (m, 4H), 2.11-1.97 (m, 2H), 1.66-1.52 (m, 2H), 0.93-0.87 (t, 3H)

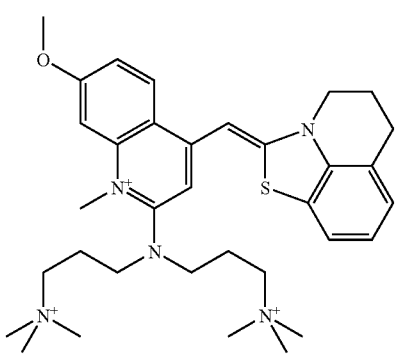 [SMILES: COc1ccc2c(/C=C3\Sc4cccc5c4N3CCC5)cc(N(CCC[N+](C)(C)C)CCC[N+](C)(C)C)[n+](C)c2c1]

2-(bis(3-(trimethylammonio)propyl)amino)-4-((5,6-dihydrothiazolo[5,4,3-ij]quinolin-2(4H)-ylidene)methyl)-7-methoxy-1-methylquinolinium (PBI 4052)

3,3'-Iminobis(N,N,N-trimethyl-1-propylammonium iodide) (530 mg, ~0.6 mmoles), 2-Chloro-4-((5,6-dihydrothiazolo[5,4,3-ij]quinolin-2(4H)-ylidene)methyl)-7-methoxy-1-methylquinolinium (60 mg, 0.14 mmoles) and triethylamine (400 μL) were dissolved in 6 mL of DMF. The reaction was kept stirring at room temperature for 3 days, and final product was purified with HPLC and about 18 mg of desired product was obtained. $^1$HNMR (d6-DMSO) δ ppm 8.61-8.56 (d, 1H), 7.77-7.73 (d, 1H), 7.35-7.21 (m, 4H), 6.80 (s, 1H), 6.70 (1H), 4.35-4.27 (t, 2H), 4.00 (s, 3H), 3.91 (s, 3H), 3.53-3.43 (t, 4H), 3.41-3.27 (m, 4H), 3.04 (s, 18H), 3.00-2.90 (t, 2H), 2.25-2.15 (m, 2H), 2.15-2.00 (m, 4H).

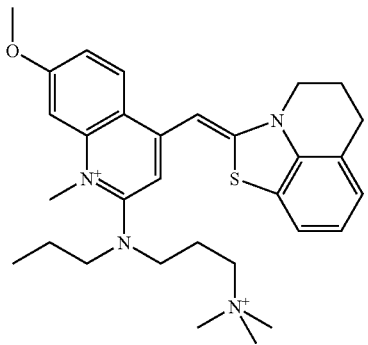 [SMILES: CCCN(CCC[N+](C)(C)C)c1cc(/C=C2\Sc3cccc4c3N2CCC4)c2ccc(OC)cc2[n+]1C]

4-((5,6-dihydrothiazolo[5,4,3-ij]quinolin-2(4H)-ylidene)methyl)-7-methoxy-1-methyl-2-(propyl(3-(trimethylammonio)propyl)amino)quinolinium 3-(propylamino)propyl-N',N',N'-trimethylammonium iodide (500 mg, ~1 mmole), 2-Chloro-4-((5,6-dihydrothiazolo[5,4,3-ij]quinolin-2(4H)-ylidene)methyl)-7-methoxy-1-methylquinolinium (60 mg, 0.14 mmoles) and triethylamine (1 mL) were dissolved in 6 mL of DMF. The reaction was kept stirring at room temperature for 24 hours, and final product was purified with HPLC and about 20 mg of desired product was obtained. $^1$HNMR (d6-DMSO) δ ppm 8.58-8.52 (d, 1H), 7.76-7.70 (d, 1H), 7.35-7.15 (m, 4H), 6.81-6.77 (s, 1H), 6.65 (s, 1H), 4.35-4.25 (t, 2H), 4.00 (s, 3H), 3.90 (s, 3H), 3.54-3.45 (t, 2H), 3.45-3.31 (m, 4H), 3.05 (s, 9H), 3.00-2.90 (t, 2H), 2.25-2.15 (m, 2H), 2.15-2.00 (m, 2H), 1.73-1.58 (m, 2H), 1.18-1.12 (t, 3H).

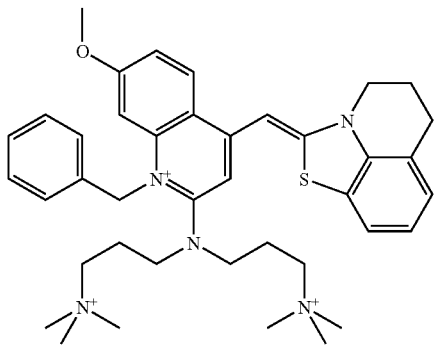 [SMILES: COc1ccc2c(/C=C3\Sc4cccc5c4N3CCC5)cc(N(CCC[N+](C)(C)C)CCC[N+](C)(C)C)[n+](Cc3ccccc3)c2c1]

1-Benzyl-2-(bis(3-(trimethylammonio)propyl) amino)-4-((5,6-dihydrothiazolo[5,4,3-ij]quinolin-2 (4H)-ylidene)methyl)-7-methoxyquinolinium (PBI 4050)

3,3'-Iminobis(N,N,N-trimethyl-1-propylammonium iodide) (410 mg, ~0.8 mmoles), 1-benzyl-2-chloro-4-((5,6-dihydrothiazolo[5,4,3-ij]quinolin-2(4H)-ylidene)methyl)-7-methoxyquinolinium chloride (44 mg, 0.08 mmoles) and triethylamine (300 μL) were dissolved in 6 mL of DMF. The reaction was kept stirring at room temperature for 24 hours, and final product was purified with HPLC and about 4 mg of desired product was obtained. $^1$HNMR (d4-MeOD) δ ppm 8.46-8.42 (d, 1H), 7.78-7.74 (d, 1H), 7.42-7.26 (m, 6H), 7.21-7.03 (m, 5H), 5.88 (s, 2H), 4.42-4.36 (t, 2H), 3.76 (s, 3H), 3.59-3.51 (t, 4H), 3.33-3.25 (m, 4H), 3.18-3.14 (m, 2H), 3.07 (s, 18H), 2.40-2.30 (m, 2H), 2.30-2.12 (m, 4H).

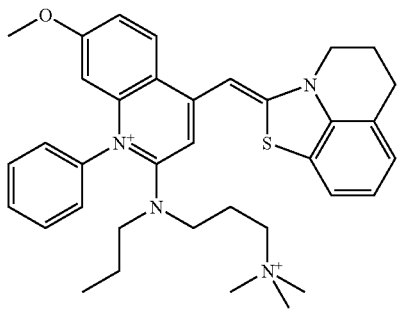 [SMILES: CCCN(CCC[N+](C)(C)C)c1cc(/C=C2\Sc3cccc4c3N2CCC4)c2ccc(OC)cc2[n+]1-c1ccccc1]

4-((5,6-dihydrothiazolo[5,4,3-ij]quinolin-2(4H)-ylidene)methyl)-7-methoxy-1-phenyl-2-(propyl(3-(trimethylammonio)propyl)amino)quinolinium (PBI 4054)

3-(propylamino)propyl-N',N',N'-trimethylammonium iodide (400 mg, ~0.8 mmoles), 2-chloro-4-((5,6-dihydrothia-zolo[5,4,3-ij]quinolin-2(4H)-ylidene)methyl)-7-methoxy-1-phenylquinolinium chloride (37 mg, 0.07 mmoles) and triethylamine (1 mL) were dissolved in 6 mL of DMF. The reaction was kept stirring at room temperature for 72 hours, and final product was purified with HPLC and about 11 mg of desired product was obtained. $^1$HNMR (d6-DMSO) δ ppm 8.65-8.59 (d, 1H), 7.90-7.64 (m, 6H), 7.36-7.20 (m, 3H), 6.93-6.91 (m, 2H), 6.76 (s, 1H), 4.42-4.34 (t, 2H), 3.69 (s, 3H), 3.25-3.05 (m, 6H), 3.05-2.90 (s, 9H), 2.28-2.16 (m, 2H), 1.74-1.68 (m, 2H), 1.36-1.20 (m, 2H), 0.80-0.72 (t, 3H)

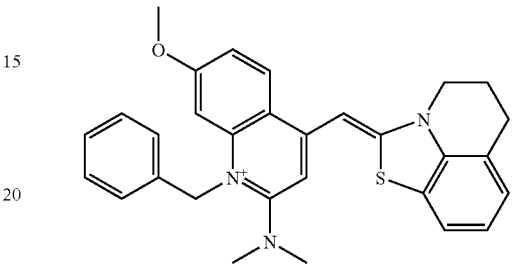

1-benzyl-4-((5,6-dihydrothiazolo[5,4,3-ij]quinolin-2 (4H)-ylidene)methyl)-2-(dimethylamino)-7-methoxyquinolinium (PBI 4051)

A similar method was used to react dimethylamine with 1-benzyl-2-chloro-4-((5,6-dihydrothiazolo[5,4,3-ij]quinolin-2(4H)-ylidene)methyl)-7-methoxyquinolinium chloride to obtain the desired compound. MS$^2$: 480. $^1$HNMR (d6-DMSO) δ ppm 8.46-8.40 (d, 1H), 7.82-7.76 (d, 1H), 7.35-7.12 (m, 7H), 7.06-6.98 (m, 3H), 6.66 (s, 1H), 5.72 (s, 2H), 4.35-4.25 (t, 2H), 3.75 (s, 3H), 3.18 (s, 6H), 3.00-2.84 (t, 2H), 2.25-2.11 (m, 2H)

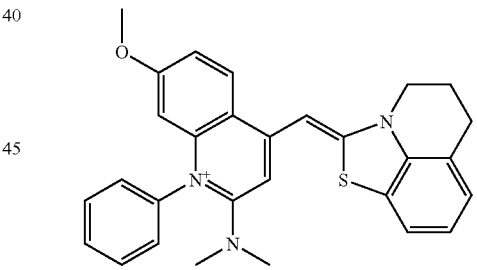

4-((5,6-dihydrothiazolo[5,4,3-ij]quinolin-2(4H)-ylidene)methyl)-2-(dimethylamino)-7-methoxy-1-phenylquinolinium (PBI 4055)

A similar method was used to react dimethylamine with 2-Chloro-4-((5,6-dihydrothiazolo[5,4,3-ij]quinolin-2(4H)-ylidene)methyl)-7-methoxy-1-phenylquinolinium chloride to obtain the desired compound. $^1$HNMR (d6-DMSO) δ ppm 8.58-8.54 (d, 1H), 7.80-7.62 (m, 6H), 7.34-7.13 (m, 3H), 6.67-6.64 (m, 2H), 6.53-6.49 (d, 1H), 4.36-4.28 (t, 2H), 3.69 (s, 3H), 3.00-2.90 (m, 2H), 2.84 (s, 6H), 2.26-2.16 (m, 2H)

The relative brightness of certain compounds (Table 2) was determined based on the protocol in Nygren, J., Svanvik, N., Kubista, M. (1998) Biopolymers, Vol. 46, 39-51, which is incorporated by reference herein.

TABLE 2

| Stain | Relative Brightness | |
|---|---|---|
| | ds DNA | ss DNA |
| SYBR Green 1 | 1 | na |
| Oli Green | 0.93 | 1 |
| 4050 | 0.63 | 1.23 |
| 4051 | 0.67 | 1.10 |
| 4052 | 0.74 | 2.41 |
| 4053 | 1.26 | 1.82 |
| 4054 | 1.19 | 3.10 |

Example 3

Analysis of Total Fluorescence for Amplification Reactions with Various Dyes

The first cycle in an amplification reaction is informative because it identifies the background (no template control; NTC), the sensitivity of detection, and the capacity for double-stranded DNA binding under various qPCR conditions (observed in reactions containing 100 ng of gDNA relative to NTC at cycle 1) in the reaction. The mathematical relationship between spectral data cycles 45:1 was used to represent dye quality.

The $B_{ds}$ ($F_M$:$F_i$) Brightness Factor is the ratio of maximum fluorescence data at 45 cycles relative to initial fluorescence of NTC at cycle 1. $F_B$, the inverse of brightness, represents "background fluorescence" expressed as a % of total double stranded fluorescence. S, relative sensitivity (almost +/− if a threshold cutoff value is identified), is a numerical representation of detection of a low level of DNA concentrations under these qPCR conditions relative to background fluorescence. $S = [Fi_{2 \mu g/ml} - Fi_{NTC}]/1\, e4$.

Materials and Methods

Reactions include NTC reactions and those having 10 pg, 1 ng, or 100 ng of human gDNA (template DNA). Amplification reactions included primers specific for Chemokine (C—C motif) ligand 18. The primer sequences were as follows in 5'-3' orientation. Forward: CACACTGATTGATCCATGCATT (SEQ ID NO: 1). Reverse: CCACCTCTTCTAAGAGTCCCAT (SEQ ID NO: 2). Data were normalized to a reference dye (ROX).

Results

For PBI 3654 (with SG control), the slope was 3.32, the y-intercept was 28.34 and $R^2$ was 0.998. $F_B$=3.6%; $F_i$=3.8 e4; $F_M$ (100 ng)=1.05 e6; and $B_{ds}$=$F_M$:$F_i$=27.7.

For PBI 3677 (with SG control), the slope was −3.35, the y=−intercept was 26.89 and $R^2$ was 0.998. $F_i$ SG NTC=7.8 e4; $F_M$ SG (100 ng)=9.9 e5; $B_{ds}$=$F_M$:$F_i$=12.7, and $F_B$ SG=7.9%.

FIG. 2 shows data for various dyes. In most cases, a detectable (<NTC) level of double stranded binding was not observed until 2 µg/mL. FIG. 3 show the change in fluorescence above baseline (ΔRmax) at 45 cycles without ROX normalization. FIG. 4 shows ΔRmax, Ct, slope, y-intercept, S, $B_{ds}$ and $F_B$ data for various dyes.

Example 4

Methods qPCR reactions (1×qPCR reaction mix; 50 µL) were assembled to contain a range of a specified dye for each run, including 0.4 µM SG as a control set in each run. The range of the test dye in a plate of reactions varied based on previous results. Reaction mix volumes with and without dye were combined in proportions to the final dye concentrations, keeping the ROX concentration uniformly distributed throughout all wells.

10 µL of serially diluted genomic DNA target or water (NTC) were combined in the reaction wells with 40 µL of reaction mix of varied [dye] for each 50 µL qPCR. The target addition offered a 10.000-fold mass range. Primers for amplification of human Chemokine (C—C motif) ligand 18 were used.

AB 7500 default cycling parameters, without the 10 minutes hot start, were employed through 45 cycles. Default SDS analysis settings were employed throughout.

qPCR reaction mix contains:
Dye plus DMSO to a constant 3% [DMSO].
$1_{POLYMERASE}$ Unit of M500/50 µl rxn (inventory $5_L$ U/µl label units=$8_P$U/µl)
20 mM Tris HCl pH 8.0
50 mM KCl
2 mM $MgCl_2$
1.6 mg/ml BSA
10% Sucrose
0.2 mM each dNTP
0.2 µM each primer
1.5 µl/ml ROX (0.075 µl/rxn).

Results

Quantitative polymerase chain reaction (qPCR) utilizes fluorescent detection to quantify the accumulation of product at each cycle during the amplification reaction. The properties of a fluorescent dye that are useful for qPCR are: low background fluorescence in the presence of single stranded DNA, an increase in fluorescence when associated with double stranded DNA, a linear relationship between the amount of double stranded DNA and fluorescence intensity, and minimal inhibition of PCR. Compounds were tested for their utility in qPCR, and a standard curve was generated using each compound. The properties of the standard curve that were used to assess the various compounds in qPCR were the slope of the standard curve (which is a measure of efficiency of the reaction), the correlation co-efficient ($R^2$) (which indicates the linearity of the data) and the y-intercept (which is a measure of sensitivity). A slope of the curve is −3.3 when the amplification reaction is 100%, an $R^2$ value of 1.0 represents perfect linearity of the data, and a higher y-intercept indicates a lower detection limit. The data is shown in FIG. 5.

Example 5

Figure 7:
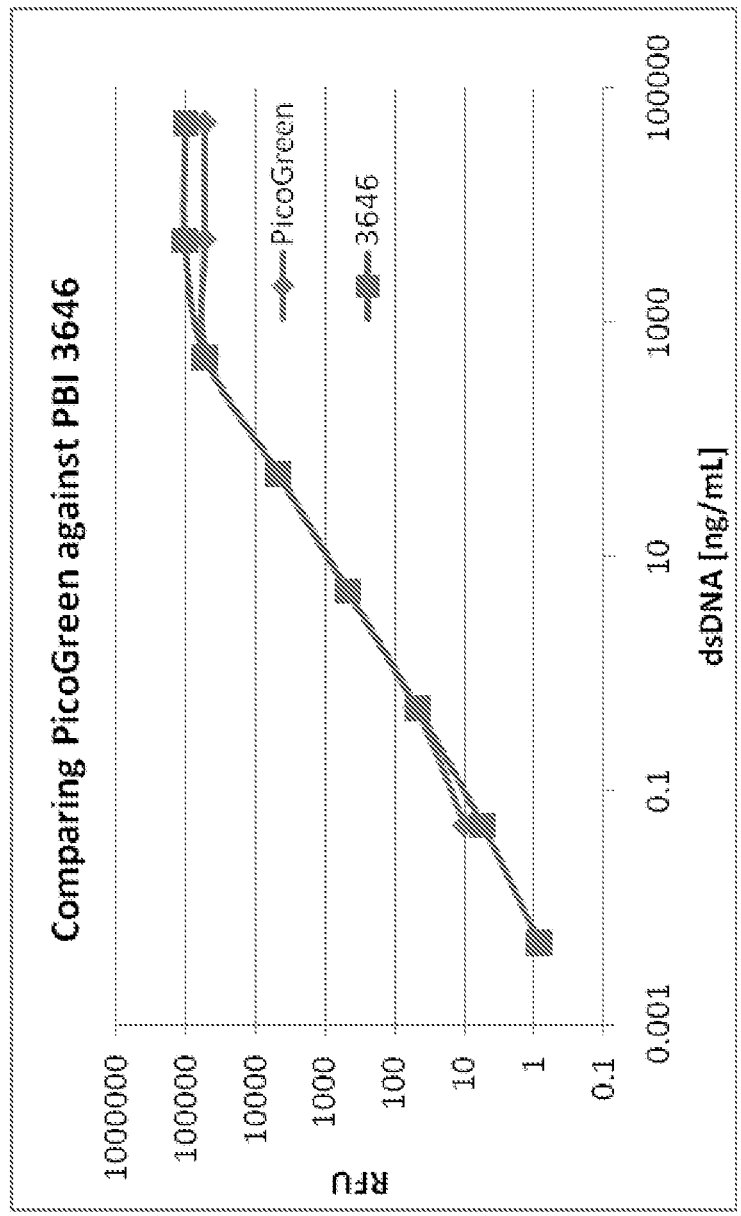
FIG. 7. Comparison of PicoGreen and PBI 3646.

10×TE (Tris, EDTA) buffer was diluted in nuclease free water to form a 1×TE buffer working solution. PBI 3646 was diluted 1:1000 in 1×TE buffer working solution. Lambda DNA was diluted in 1×TE buffer working solution to form a working solution of 2000 ng/mL. 1:10 fold dilutions of lambda DNA were performed in 1×TE buffer working solution to generate standard curves. 100 µL of serial diluted lambda DNA was transferred to a black 96 well microliter plate. 100 µL of PBI 3646 working solution was added to each well. The solutions were mixed gently. The plate was protected from light and incubated for 5 minutes. The fluorescence was measured on a GloMax Multi+ using a blue optical kit (Ex. 490 nm, Em. 515-570 nm). For data analysis, background values for lamda DNA solution were subtracted from all sample values. Results are shown in FIG. 7.

All publications, patents and patent applications are incorporated herein by reference. While in the foregoing specification, this invention has been described in relation to certain preferred embodiments thereof, and many details have been set forth for purposes of illustration, it will be apparent to those skilled in the art that the invention is susceptible to additional embodiments and that certain of the details herein may be varied considerably without departing from the basic principles of the invention.

What is claimed is:

1. A compound of Formula I:

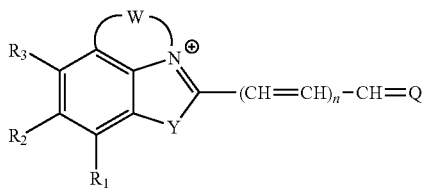

wherein $R^1$, $R^2$ and $R^3$ are each H

Y is S or O;

W taken together with the atoms to which it is attached is a 6 membered heterocyclic ring;

n is 0;

Q is Q2:

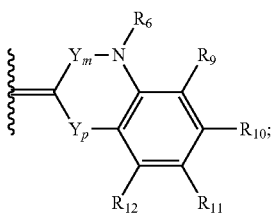

wherein

Y is $-CR^{13}=CR^{14}-$; m is 1 and p is 0;

$R^6$ is unsubstituted ($C_1$-$C_8$)alkyl, unsubstituted aryl, or unsubstituted ($C_1$-$C_8$)alkaryl;

$R^9$, $R^{11}$, and $R^{12}$ are each independently H, amino, or halo;

$R^{10}$ is H, methoxy, amino or halo;

one of $R^{13}$ and $R^{14}$ is H and the other is $NR^{15}R^{16}$;

$R^{15}$ is ($C_1$-$C_6$)alkyl or ($C_1$-$C_6$)alkyl-$NR^{17}R^{18}$ or $C_3H_7N^+(CH_3)_3$, wherein $R^{17}$ and $R^{18}$ are each independently H or ($C_1$-$C_6$)alkyl; and $R^{16}$ is ($C_1$-$C_6$)alkyl-$NR^{17}R^{18}$ or $C_3H_7-N^+(CH_3)_3$, wherein $R^{17}$ and $R^{18}$ are each independently H or ($C_1$-$C_6$)alkyl;

or a salt thereof.

2. The compound of claim 1 wherein $R^1$, $R^2$ and $R^3$ are each H; Y is S; and n is 0.

3. The compound of claim 1 wherein Q is Q2; m is 1; $R^6$ is methyl, ethyl, propyl, phenyl, benzyl, 2-phenylethyl, or 3-phenylpropyl; $R^9$, $R^{10}$, $R^{11}$, and $R^{12}$ are each H; $R^{13}$ is H; $R^{14}$ is $NR^{15}R^{16}$ wherein $R^{15}$ is methyl, ethyl, propyl, or butyl.

4. The compound of claim 3 wherein $R^{16}$ is ($C_1$-$C_3$)alkyl-$N(Me)_2$.

5. The compound of claim 1 wherein the compound is a compound of formula II:

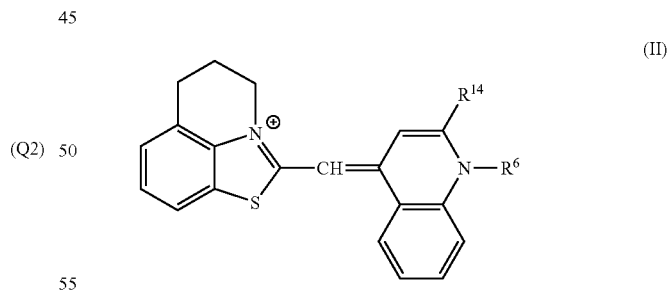

wherein $R^6$ is methyl, ethyl, propyl, phenyl, benzyl, 2-phenylethyl, or 3-phenylpropyl; and $R^{14}$ is

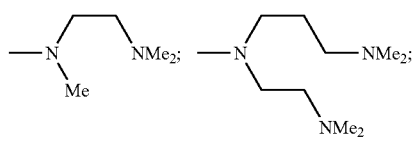

-continued
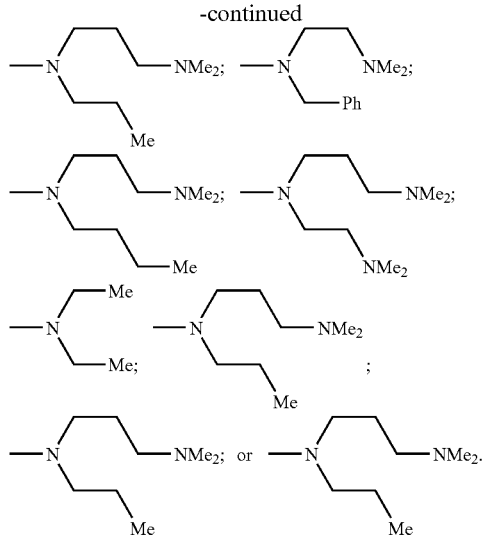
6. The compound of claim 1 wherein the compound displays enhanced emission in the presence of nucleic acids, in either in vitro or in vivo environments, compared to its emission in the same environment lacking nucleic acids.
* * * * *

SEQUENCE LISTING

<160> NUMBER OF SEQ ID NOS: 2

<210> SEQ ID NO 1
<211> LENGTH: 22
<212> TYPE: DNA
<213> ORGANISM: Artificial Sequence
<220> FEATURE:
<223> OTHER INFORMATION: Synthetic Oligonucleotide

<400> SEQUENCE: 1
cacactgatt gatccatgca tt                                              22

<210> SEQ ID NO 2
<211> LENGTH: 22
<212> TYPE: DNA
<213> ORGANISM: Artificial Sequence
<220> FEATURE:
<223> OTHER INFORMATION: Synthetic Oligonucleotide

<400> SEQUENCE: 2
ccacctcttc taagagtccc at                                              22